United States Patent [19]
Khan et al.

[11] Patent Number: 5,821,356
[45] Date of Patent: Oct. 13, 1998

[54] PROPARGYLETHOXYAMINO NUCLEOTIDES

[75] Inventors: Shaheer H. Khan, Foster City; Steven M. Menchen, Fremont; Barnett B. Rosenblum, San Jose, all of Calif.

[73] Assignee: The Perkin Elmer Corporation, Foster City, Calif.

[21] Appl. No.: 696,808

[22] Filed: Aug. 13, 1996

Related U.S. Application Data

[63] Continuation-in-part of Ser. No. 694,442, Aug. 12, 1996, abandoned.

[51] Int. Cl.$^6$ .................................................. C07H 19/00
[52] U.S. Cl. ................... 536/26.26; 536/26.3; 536/26.6; 536/26.7; 536/26.74; 536/26.8; 536/27.1; 536/27.13; 536/27.21; 536/27.6; 536/27.8; 536/27.81; 536/28.1; 536/28.3; 536/28.4; 536/28.53; 536/28.54
[58] Field of Search ................................ 536/26.26, 26.3, 536/26.7, 26.74, 26.8, 27.1, 27.13, 27.21, 27.6, 27.8, 27.81, 28.1, 28.3, 28.4, 28.5, 28.53, 28.54, 26.6; 435/6, 89, 90, 91.1–91.53

[56] References Cited

U.S. PATENT DOCUMENTS

| | | | |
|---|---|---|---|
| 4,318,849 | 3/1982 | Bühlerl et al. | 260/148 |
| 4,879,214 | 11/1989 | Kornher et al. | |
| 5,047,519 | 9/1991 | Hobbs, Jr. et al. | 536/27.14 |
| 5,151,507 | 9/1992 | Hobbs, Jr. et al. | 536/27.14 |
| 5,171,534 | 12/1992 | Smith et al. | 435/6 |
| 5,188,934 | 2/1993 | Menchen et al. | 435/6 |
| 5,366,860 | 11/1994 | Bergot et al. | 435/6 |

FOREIGN PATENT DOCUMENTS

| | | | |
|---|---|---|---|
| 0251786 | 1/1988 | European Pat. Off. | C07D 403/04 |
| WO93/24511 | 12/1993 | WIPO | C07H 21/02 |
| WO94/17092 | 8/1994 | WIPO | C07H 21/00 |
| WO95/18139 | 7/1995 | WIPO | C07H 21/00 |

OTHER PUBLICATIONS

Livak et al., "Detectiton of single base differences using biotinylated nucleotides with very long linker arms," *Nucleic Acids Research* 20(18):4831–4837 (Aug. 12, 1992).
Kornher et al., "Mutation detection using nucleotide analogs that alter electrophoretic mobility," *Nucleic Acids Research* (17(19) (1989).

Primary Examiner—James O. Wilson
Attorney, Agent, or Firm—Paul D. Grossman

[57] ABSTRACT

Propargylethoxyamino nucleosides are disclosed having the structure

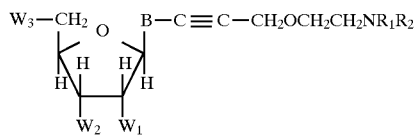

wherein $R_1$ and $R_2$ are —H, lower alkyl, or label; B is a 7-deazapurine, purine, or pyrimidine nucleoside base; $W_1$ is —H or —OH; $W_2$ is —OH or a moiety which renders the nucleoside incapable of forming a phosphodiester bond at the 3'-position; and $W_3$ is —$PO_4$, —$P_2O_7$, —$P_3O_{10}$, phosphate analog, or —OH. Additionaly, a primer extension method is provided employing the above propargylethoxyamino nucleosides.

8 Claims, 15 Drawing Sheets

6-FAM-ddATP 1 pm

Dye Terminator

Dye Primer

6-FAM-ddATP 4 pm

Dye Terminator

Dye Primer

6-FAM-ddATP 150 pm

Terminator Dye

Primer Dye

6-FAM-ddCTP 250 pm

6-FAM-EO-ddCTP 50 pm

DTAMRA-1-labeled ddCTP using a propargylamido linker

DTAMRA-2-labeled ddCTP using a propargyl-1-ethoxyamido linker

PROPARGYLETHOXYAMINO NUCLEOTIDES

This is a CIP of U.S. application Ser. No. 694,442 filed Aug. 12, 1996, now abandoned.

FIELD OF THE INVENTION

This invention relates generally to nucleotide compounds useful as substrates for polymerase enzymes and polynucleotides derived therefrom. More specifically, this invention relates to propargylethoxyamino nucleotides and their use in preparing fluorescently-labeled nucleotides useful as substrates for thermostable polymerases, especially their use in preparing fluorescently-labeled nucleotides as chain-terminating substrates in a fluorescence-based DNA sequencing method.

REFERENCES

[F]dNTP Reagents Protocol, PE Applied Biosystems, Revision A, p/n 402774 (March 1996)
ABI PRISM™ 373 DNA Sequencing System User's Manual, p/n 903204 (June 1994)
ABI PRISM™ Dye Primer Cycle Sequencing Core Kit with AmpLitaQ™ DNA Polymerase, FS, Protocol, Revision C, p/n 402114 (1996)
ABI PRISM™ Dye Terminator Cycle Sequencing Core Kit Protocol, PE Applied Biosystems, Revision A, p/n 402116 (August 1995)
Benson et al., U.S. patent application Serial No. 08/626,085 filed April 1, 1996
Bergot, et al., U.S. Pat. No. 5,366,860 (1994)
Connell et al., Biotechniques, 5(4): 342–348 (1987)
Eckstein ed., Oligonucleotides and Analogs, Chapters 8 and 9, IRL Press (1991)
Eckstein et al., Nucleic Acids Research, 16(21): 9947–59 (1988)
Gish et al, Science, 240: 1520 (1988)
Hermanson, Bioconjugate Techniques, Academic Press (1996)
Hobbs, et al., U.S. Pat. No. 5,151,507 (1992)
Kasai, et al., Anal. Chem., 47: 34037 (1975)
Khanna, et al., U.S. Pat. No. 4,318,846 (1988)
Lee et al, Nucleic Acids Research, 20(10): 2471–2483 (1992)
Menchen et al, U.S. Pat. No. 5,188,934 (1993)
Murray, Nucleic Acids Research, 17(21): 8889 (1989)
Prober et al., Science, 238: 336–341 (1987)
Sanger, et al., Proc. Nail. Acad Sci., 74: 5463–5467 (1977)
Scheit, Nucleofide Analogs, John Wiley (1980)
Shaw et al., Nucleic Acids Research, 23: 4495–4501 (1995).
Smith et al., U.S. Pat. No. 5,171,534 (1992)
Stryer, Biochemistry, W. H. Freeman (1981)
Trainor, Anal. Chem., 62: 418–426 (1990)

BACKGROUND

DNA sequencing has become a vitally important technique in modern biology and biotechnology, providing information relevant to fields ranging from basic biological research to drug discovery to clinical medicine. Because of the large volume of DNA sequence data to be collected, automated techniques have been developed to increase the throughput and decrease the cost of DNA sequencing methods (Smith; Connell; Trainor).

A preferred automated DNA sequencing method is based on the enzymatic replication technique developed by Sanger (Sanger). In Sanger's technique, the DNA sequence of a single-stranded template DNA is determined using a DNA polymerase to synthesize a set of polynucleotide fragments wherein the fragments (i) have a sequence complementary to the template sequence, (ii) vary in length by a single nucleotide, and (iii) have a 5'-end terminating in a known nucleotide, e.g., A, C, G, or T. In the method, an oligonucleotide primer is annealed to a 3'-end of a template DNA to be sequenced, the 3'-end of the primer serving as the initiation site for polymerase-mediated polymerization of a complementary polynucleotide fragment. The enzymatic polymerization step is carried out by combining the template-primer hybrid with the four natural deoxynucleotides "dNTPs"), a DNA polymerase enzyme, and a 2',3'-dideoxynucleotide triphosphate ("ddNTP") "terminator". The incorporation of the terminator forms a fragment which lacks a hydroxy group at the 3'-terminus and thus can not be further extended, i.e., the fragment is "terminated". The competition between the ddNTP and its corresponding dNTP for incorporation results in a distribution of different-sized fragments, each fragment terminating with the particular terminator used in the reaction. To determine the complete DNA sequence of the template, four parallel reactions are run, each reaction using a different ddNTP terminator. To determine the size distribution of the fragments, the fragments are separated by electrophoresis such that fragments differing in size by a single nucleotide are resolved.

In a modern variant of the classical Sanger technique, the nucleotide terminators are labeled with fluorescent dyes (Prober; Hobbs), and a thermostable DNA polymerase enzyme is used Murray). Several advantages are realized by utilizing dye-labeled terminators: (i) problems associated with the storage, use and disposal of radioactive isotopes are eliminated; (ii) the requirement to synthesize dye-labeled primers is eliminated; and, (iii) when using a different dye label for each A,G,C, or T nucleotide, all four reactions can be performed simultaneously in a single tube. Using a thermostable polymerase enzyme (i) permits the polymerization reaction to be run at elevated temperature thereby disrupting any secondary structure of the template resulting in less sequence-dependent artifacts, and (ii) permits the sequencing reaction to be thermocycled, thereby serving to linearly amplify the amount of extension product produced, thus reducing the amount of DNA template required to obtain a sequence.

While these modern variants on Sanger sequencing methods have proven effective, several problems remain with respect to optimizing their performance and economy. One problem encountered when using dye-labeled terminators in combination with thermostable polymerase enzymes, particularly in the case of fluorescein-type dye labels, is that a large excess of dye-labeled terminator over the unlabeled dNTs is required, up to a ratio of 50:1. This large excess of labeled terminator makes it necessary to purify the sequencing reaction products prior to performing the electrophoretic separation step. This clean-up step is required in order to avoid interference caused by the comigration of unincorporated labeled terminator species and bona fide sequencing fragments. A typical clean-up method includes an ethanol precipitation or a chromatographic separation (ABI PRISM™ Dye Terminator Cycle Sequencing Core Kit Protocol). Such a clean-up step greatly complicates the task of developing totally automated sequencing systems wherein the sequencing reaction products are transferred directly into an electrophoretic separation process. A second problem encountered when using presently available dye-labeled terminators in combination with a thermostable polymerase is that an uneven distribution of peak heights is obtained in Sanger-type DNA sequencing.

SUMMARY

The present invention is directed towards our discovery of a novel class of propargylethoxyamino nucleotides useful as chain-terminating dideoxynucleotides, and, as chain-extending deoxynucleotides, in a primer extension reaction, e.g., in a Sanger-type DNA sequencing or in a PCR reaction.

It is an object of the invention to provide a nucleotide which can be used to form a labeled chain-terminating nucleotide.

It is a further object of the invention to provide a chain-terminating nucleotide which includes a label.

It is yet an additional object of the invention to provide a chain-terminating nucleotide which includes a fluorescent label wherein a reduced excess concentration of such labeled chain-terminating nucleotide over an unlabeled chain-terminating nucleotide is required in a Sanger-type DNA sequencing process.

It is another object of the invention to provide a labeled chain-terminating nucleotide which results in a more even distribution of peak heights in a Sanger-type DNA sequencing process.

It is an object of the invention to provide a nucleotide which can be used to form a labeled chain-extending deoxynucleotide.

It is a further object of the invention to provide a chain-extending deoxynucleotide which includes a label.

It is an additional object of the invention to provide methods including a primer extension reaction utilizing the propargylethoxyamino nucleotides of the invention.

In a first aspect, the foregoing and other objects of the invention are achieved by a nucleoside compound having the structure:

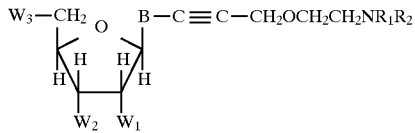

wherein the variable substituents $R_1$–$R_2$ and $W_1$–$W_3$ are defined as follows. $R_1$ and $R_2$ taken separately are —H, lower alkyl protecting group, or label. In a preferred embodiment, one of $R_1$ and $R_2$ is label, the label preferably being a fluorescein-type dye or a rhodamine-type dye. B is a 7-deazapurine, purine, or pyrimidine nucleoside base, preferably uracil, cytosine, 7-deazaadenine, or 7-deazaguanosine. When B is purine or 7-deazapurine, the sugar moiety is attached at the $N^9$-position of the purine or deazapurine, and when B is pyrimidine, the sugar moiety is attached at the $N^1$-position of the pyrimidine. When B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine. $W_1$ is —H or —OH. $W_2$ is —OH or a moiety which renders the nucleoside incapable of forming a phosphodiester bond at the 3'-position. $W_3$ is —$PO_4$, —$P_2O_7$, —$P_3O_{10}$, phosphate analog, or —OH.

In a second aspect, the invention includes a method for performing a primer extension reaction including the following steps: providing a template nucleic acid; annealing an oligonucleotide primer to a portion of the template nucleic acid; and adding primer-extension reagents to the primer-template hybrid for extending the primer. In an important aspect of the invention, the primer extension reagents include a propargylethoxyamino nucleoside compound having the structure described above.

DETAILED DESCRIPTION OF THE PREFERRED EMBODIMENTS

Figure 1A:
FIG. 1A shows results from a Terminator Titration Assay using 1 pmol of dye-labeled terminator.
Figure 1A:
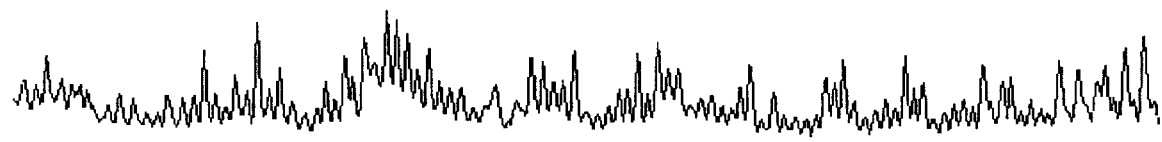

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises a novel class of propargylethoxyamino nucleoside compounds useful as substrates for polymerase enzymes. The compounds of the present invention find particular application as labeled dideoxynucleotide chain-terminating agents for use in Sanger-type DNA sequencing methods, and, as labeled deoxynucleotide chain-extending agents for use in methods including a primer extension reaction, e.g., PCR.

The invention is based in part on the discovery that the subject dye-labeled nucleotides are particularly good substrates for thermostable DNA polymerase enzymes, e.g., a significantly reduced molar excess is required in a Sanger-type DNA sequencing reaction relative to that required when using currently available dye-labeled terminators.

I. DEFINITIONS

Unless stated otherwise, the following terms and phrases as used herein are intended to have the following meanings:

The term "lower alkyl" denotes straight-chain and branched hydrocarbon moieties containing from 1 to 8 carbon atoms, i.e., methyl, ethyl, propyl, isopropyl, tert-butyl, isobutyl, sec-butyl neopentyl, tert-pentyl, and the like.

The term "label" refers to a moiety that, when attached to the nucleosides of the invention, render such nucleosides, and polynucleotides containing such nucleotides, detectable using known detection means. Exemplary labels include fluorophores, chromophores, radioisotopes, spin-labels, enzyme labels, chemiluminescent labels, and the like, which allow direct detection of a labeled compound by a suitable detector, or, a ligand, such as an antigen, or biotin, which can bind specifically with high affinity to a detectable antiligand, such as a labeled antibody or avidin. Preferably the labels are fluorescent dyes such as fluorescein-type or rhodamine-type dyes (Lee; Menchen).

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms (Stryer). The term "nucleotide" as used herein refers to a phosphate ester of a nucleoside, e.g., triphosphate esters, wherein the most common site of esterification is the hydroxyl group attached at the C-5 position of the pentose. Many times in the present disclosure the term nucleoside will be intended to include both nucleosides and nucleotides. "Analogs" in reference to nucleosides include synthetic analogs having modified base moieties, modified sugar moieties, and/or modified phosphate ester moieties, e.g., as described elsewhere (Scheit; Eckstein 1991).

As used herein, the terms "polynucleotide" or "oligonucleotide" refer to linear polymers of natural nucleotide monomers or analogs thereof including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., H, NH$_4$, Na, and the like if such counterions are present. Polynucleotides typically range in size from a few monomeric units, e.g. 8–40, to several thousands of monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted.

The term "phosphate analog" refers to analogs of phosphate wherein the phosphorous atom is in the +5 oxidation state and one or more of the oxygen atoms is replaced with a non-oxygen moiety, exemplary analogs including phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, NH$_4$, Na, and the like if such counterions are present.

As used herein, the term "propargylamido linker" shall refer to a linker having the structure

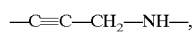

the term "propargyl-1-ethoxyamido linker" shall refer to a linker having the structure

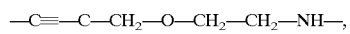

and the term "propargyl-2-ethoxyamido linker" shall refer to a linker having the structure

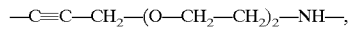

where, for each of the above structures, the terminal end of the acetylene is bound to a nucleotide base, and the amide nitrogen is bound through a convenient linkage to a label.

The term "fluorescein-type dyes" refers to a class of xanthene dye molecules which include the following fused three-ring system:

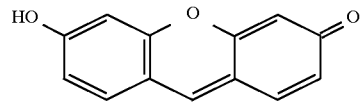

where a wide variety of substitutions are possible at each deoxy ring position. A particularly preferred subset of fluorescein-type dyes include the 4,7,-dichorofluoresceins (Menchen). Examples of fluorescein-type dyes used as fluorescent labels in DNA sequencing methods include 6-carboxyfluorescein (6-FAM, 5-carboxyfluorescein (5-FAM), 6-carboxy-4,7,2',7'-tetrachlorofluorescein (TET), 6-carboxy-4,7,2',4',5',7'-hexachlorofluorescein (HEX), 5-(and 6)carboxy-4',5'-dichloro-2'7'-dimethoxyfluorescein (JOE), and 5-carboxy-2',4',5',7'-tetrachlorofluorescein (ZOE). Many times the designation -1 or -2 is placed after an abbreviation of a particular dye, e.g., HEX-1. The "-1" and "-2" designations indicate the particular dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1M triethylammonium acetate to 35% acetonitrile/65% 0.1M triethylammonium acetate.

The term "rhodamine-type dyes" refers to a class of xanthene dye molecules which include the following fused three-ring system:

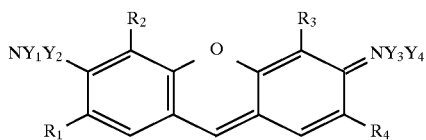

where preferably $Y_1-Y_4$ taken separately are hydrogen or lower alkyl, or, when taken together, $Y_1$ and $R_2$ is propano and $Y_2$ and $R_1$ is propano, or, when taken together, $Y_3$ and $R_3$ is propano and $Y_4$ and $R_4$ is propano. A wide variety of substitutions are possible at each deoxy ring position including the $R_1-R_4$ positions. Exemplary rhodamine type dyes useful as nucleoside labels include tetramethylrhodamine (TAMRA), 4,7-diclorotetramethyl rhodamine (DTAMRA), rhodamine X (ROX), rhodamine 6G (R6G), rhodamine 110 (R110), and the like (Bergot; Lee).

As used herein, the term "FLAN dyes" referes to asymmetric benzoxanthene dye compounds having the formula:

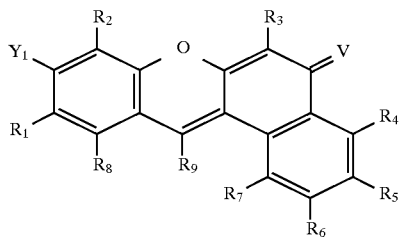

wherein $Y_1$ and $Y_2$ taken separately are hydroxyl, oxygen, imminium, or amine. $R_1-R_8$ taken separately are hydrogen, fluorine, chlorine, lower alkyl, lower alkene, lower alkyne, sulfonate, amino, ammonium, amido, nitrile, alkoxy, linking group, or combinations thereof. And, $R_9$ is acetylene, alkane, alkene, cyano, substituted phenyl, or combinations thereof the substituted phenyl having the structure:

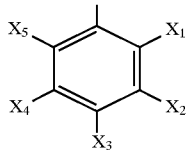

wherein $X_1$ is carboxylic acid or sulfonic acid; $X_2$ and $X_5$ taken separately are hydrogen, chlorine, fluorine, or lower alkyl; and $X_3$ and $X_4$ taken separately are hydrogen, chlorine, fluorine, lower alkyl carboxylic acid, sulfonic acid, or linking group (Benson).

As used herein the term "primer-extension reagent" means a reagent including components necessary to effect the enzymatic template-mediated extension of an oligonucleotide primer. Primer extension reagents include: (i) a polymerase enzyme, e.g., a thermostable polymerase enzyme such as Taq polymerase; (ii) a buffer; (iii) deoxynucleotide triphosphates, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of DNA sequencing reactions, (iv) dideoxynucleotide triphosphates, e.g., dideoxyguanosine 5'-triphosphate, 7-deazadideoxyguanosine 5'-triphosphate, dideoxyadenosine 5'-triphosphate, dideoxythymidine 5'-triphosphate, and dideoxycytidine 5'-triphosphate.

"Template nucleic acid" refers to any nucleic acid which can be presented in a single stranded form and is capable of annealing with a primer oligonucleotide. Exemplary template nucleic acids include DNA, RNA, which DNA or RNA may be single stranded or double stranded. More particularly, template nucleic acid may be genomic DNA, messenger RNA, cDNA, DNA amplification products from a PCR reaction, and the like. Methods for preparation of template DNA may be found elsewhere (ABI PRISM™ Dye Primer Cycle Sequencing Core Kit).

II. PROPARGYLETHOXYAMINO NUCLEOTIDE COMPOUNDS

In a first aspect, the present invention comprises a novel class of propargylethoxyamino nucleoside compounds having the general structure shown immediately below as Formula I. (Note that all molecular structures provided throughout this disclosure are intended to encompass not only the exact electronic structure presented, but also include all resonant structures and protonation states thereof.)

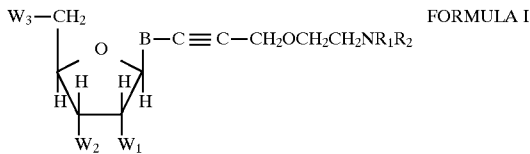

FORMULA I

Referring to Formula I, $R_1$ and $R_2$ are chosen from among —H, lower alkyl, protecting group, or label. Preferably, the label is a fluorescent dye. More preferably the label is a fluorescein-type fluorescent dye or a rhodamine-type fluorescent dye. Preferably, when one of $R_1$ and $R_2$ is a label, the other is either —H or lower alkyl. Preferred protecting groups include acyl, alkoxycarbonyl, or sulfonyl. More preferably, the protecting group is trifluoroacetyl.

The label is attached to the nucleoside through a "linkage" typically formed by the reaction of the primary or secondary amino moiety of the propargylethoxyamino nucleoside with a "complementary functionality" located on the label. Preferably, the complementary functionality is isothiocyanate, isocyanate, acyl azide, N-hydroxysuccinimide (NHS) ester, sulfonyl chloride, aldehyde or glyoxal, epoxide, carbonate, aryl halide, imidoester, carbodiimide, anhydride, 4,6-dichlorotriazinylamine, or other active carboxylate (Hermanson). In a particularly preferred embodiment, the complementary functionality is an activated NHS ester which reacts with the amine of the propargylethoxyamino nucleoside of the invention, where to form the activated NHS ester, a label including a carboxylate complementary functionality is reacted with dicyclohexylcarbodiimide and N-hydroxysuccinimide to form the NHS ester (Khanna; Kasai). Table 1 below shows a sampling of representative complementary functionalities and resulting linkages formed by reaction of the complementary functionality with the amine of the propargylethoxyamino nucleoside.

TABLE 1

| Complementary Functionality | Linkage |
|---|---|
| —NCS | —NHCSNH— |
| —NH—C(=N-)(N=)(N-Cl)(N-Cl) (triazine with 2 Cl) | —NH—C(=N-)(N=)(N-Cl)(NH—) (triazine with 1 Cl, 1 NH) |
| —SO$_2$X | —SO$_2$NH— |
| —C(=O)—O—N(succinimidyl) | —C(=O)—NH— |

Again referring to Formula I, B is a 7-deazapurine, purine, or pyrimidine nucleotide base, where in a preferred embodiment, B is chosen from the group consisting of uracil, cytosine, 7-deazaadenine, and 7-deazaguanosine. When B is purine or 7-deazapurine, the sugar moiety of the nucleotide is attached at the $N^9$-position of the purine or deazapurine, and when B is pyrimidine, the sugar moiety is attached at the $N^1$-position of the pyrimidine. When B is a purine, the adjacent triple-bonded carbon is attached to the 8-position of the purine, and when B is 7-deazapurine, the adjacent triple-bonded carbon is attached to the 7-position of the 7-deazapurine, and when B is pyrimidine, the adjacent triple-bonded carbon is attached to the 5-position of the pyrimidine.

$W_1$ is selected from among —H and —OH. When $W_1$ is —OH the nucleoside is a ribonucleotide, and when $W_1$ is —H the nucleoside is a deoxyribonucleotide.

$W_2$ is —OH or a moiety which renders the nucleoside incapable of forming a phosphodiester bond at the 3'-position. Preferred moieties useful for this function include —H, azido, amino, fluro, methoxy, and the like.

$W_3$ is selected from the group consisting of —PO$_4$, —P$_2$O$_7$, —P$_3$O$_{10}$, phosphate analog, and —OH. In a preferred embodiment useful for enzymatic synthesis of polynucleotides, $W_3$ is —P$_3$O$_{10}$.

Generally, the propargylethoxyamino nucleosides of the invention are prepared as follows. Bromoethanol is reacted with potassium phthalimide to give a phthalimido derivative. The phthalimido derivative is then O-alkylated with propargyl bromide in the presence of NaH, resulting in a protected 3-(2-phthalimidoethoxy)propyne linking arm. An iodo-nucleoside is then reacted with the protected linking arm in the presence of cuprous iodide, tetrakis (triphenylphosphine)palladium, and triethylamine in dimethylformamide for approximately 12 hours at ambient temperature or until the reaction is complete as determined by TLC. The solution is then concentrated in vacuo and the product is purified by silica gel flash chromatography and is analyzed for identity and purity by proton NMR and analytical reverse-phase HPLC (C-18 column). Treatment with ethylenediamine, followed by acetylation with ethyl trifluoroacetate, gave a nucleoside-linking arm compound. Freshly distilled phosphorous oxychloride is added to the nucleoside-linking arm compound in trimethylphosphate at −30° C. to form the corresponding dichloromonophosphate. The reaction mixture is quenched with 2M tetraethylammonium bicarbonate (TEAB) pH 8.0 to yield the monophosphate, which is then purified by preparative reverse-phase (C-18 column). The monophosphate is activated with carbonyldiimidazole (CDI) and excess CDI is quenched with MeOH. The activated monophosphate is reacted, at room temperature, with tributylammonium pyrophosphate. When complete, the reaction is quenched with 0.2M TEAB and purified by reverse phase HPLC (C-18 column). The purified protected triphosphate is evaporated to dryness and resuspended in concentrated aqueous NH$_4$OH to remove the TFA group. The deprotected triphosphate solution is evaporated to dryness and formulated with 0.1M TEAB pH 7.0 to a desired concentration. The concentration and purity of the formulated bulk are confirmed by UV/Vis spectroscopy and ion-pairing HPLC respectively.

Generally, in a preferred method, dye-labeled propargylethoxyamino nucleosides of the invention are prepared as follows. A propargylethoxyamino nucleoside is dissolved in 100 mM TEAB (pH 7.0), the solution is evaporated to dryness, and the nucleoside is resuspended in 250 mM sodium bicarbonate buffer (pH 9.0). Dye-NHS (in DMSO) is added and allowed to react overnight with stirring. When complete, the reaction mixture is purified by an ion exchange and reverse phase HPLC (C-18 column). The dye labeled triphosphate nucleotide solution is evaporated to dryness and formulated with 50 mM 3-[cyclohexylamino]-2-hydroxy-1-propane-sulfonic acid (CAPSO) pH 9.6 to a desired concentration. The concentration and purity of the formulated bulk are confirmed by UV/Vis spectroscopy and ion-pairing HPLC, respectively.

III. METHODS UTILIZING THE PROPARGYLETHOXYAMINO COMPOUNDS

The propargylethoxyamino compounds of the invention are particularly well suited for use in methods which include a template-mediated primer extension reaction of the type including the following steps: (i) providing a template nucleic acid; (ii) annealing an oligonucleotide primer to a portion of the template nucleic acid thereby forming a primer-template hybrid; and (iii) adding primer-extension reagents to the primer-template hybrid for extending the primer. In particular, the compounds of the invention provide a means for incorporating a label directly into a primer extension product.

In a first preferred class of methods utilizing a primer extension reaction, the extension products are labeled by including labeled deoxynucleotide triphosphates or deoxyribonucleoside triphosphates of the invention into the primer extension reaction thereby randomly incorporating labels throughout the extension product ([F]dNTP Reagents Protocol). Such a method can be used to label PCR amplicons as well as single-primer derived extension products. To label an extension product in this way, the primer extension reaction is performed using established protocols, but a labeled deoxynucleotide triphosphate is added to the reaction. Generally, to perform a primer extension reaction in the context of PCR, template nucleic acid is mixed with 20 pmol of each primer and primer-extension reagents comprising 20 mM buffer at pH 8, 1.5 mM MgCl$_2$, 50 mM of each deoxynucleotide triphosphate (dNTP), and 2 units of Taq polymerase or other suitable thermostable polymerase. The reaction mixture is then thermocycled, a typical thermocycle profile comprising a denaturation step (e.g. 96° C., 15 s), a primer annealing step (e.g., 55° C., 30 s), and a primer extension step (e.g., 72° C., 90 s). Typically, the thermocycle is repeated from about 10 to 40 cycles. For PCR amplifications, the typical ratio of labeled deoxynucleotide triphosphate to unlabeled deoxynucleotide triphosphate is between 100:1 to 1000:1, depending on the amount of signal desired. The maximum ratio of labeled deoxynucleotide triphosphate to unlabeled deoxynucleotide triphosphate that can be used in a PCR reaction mixture without adversely affecting amplification efficiency is approximately 1:4.

In a second preferred class of methods utilizing a primer extension reaction, the extension products are labeled by including labeled dideoxynucleotide triphosphates or dideoxyribonucleoside triphosphates of the invention into the primer extension reaction thereby randomly incorporating detectable labels at the 3'-terminal nucleotide, e.g., Sanger-type DNA sequencing. Generally, to perform a primer extension reaction in the context of Sanger-type DNA sequencing using labeled dideoxynucleotide triphosphates of the invention, 1 µl of template solution (1 ml of PCR reaction diluted with 5 ml water) and 2 µl of primer (0.4 pmol/µl) is mixed with primer-extension reagents comprising 2 µl buffer (400 mM Tris-HCl, 10 mM MgCl$_2$, pH 9.0.), 2 µl of a deoxynucleotide/labeled dideoxynucleotide mixture (T-termination reaction, 1250 µM ddTTP, 250 µM dATP, 250 µM dCTP, 180 µM7-deaza-dGTP, and 250 µM dTTP), and 2 µl of polymerase enzyme (5 Units/µl where one unit is defined as in Lawyer). The reaction is then thermocycled using the following exemplary program: denaturation at 98° C. for 5 s followed by repeated cycles of 96° C. for 5 s; 55° C. for 40 s; 68° C. for 1 min, where the cycle is repeated approximately 15 times.

The propargylethoxyamino compounds of the invention may also be used in the context of variants of Sanger-type sequencing methods which rely on base-specific cleavage of the primer extension products, e.g., methods utilizing labile nucleotides (Eckstein 1988; Shaw).

IV. EXAMPLES

The invention will be further clarified by a consideration of the following examples, which are intended to be purely exemplary of the invention and not to in any way limit its scope.

Example 1

Terminator Titration Assay for Determining the Required Terminator Excess in a Sequencing Reaction The Terminator Titration Assay was used to determine the minimum amount of dye terminator required to create a full sequencing ladder, i.e., a sequencing ladder including all fragments terminating in a particular base having a length of between about 20 to about 600 nucleotides. The key components of the assay were (i) a primer labeled with a first dye, and (ii) a terminator labeled with a second dye spectrally resolvable from the first dye. In the assay, when an insufficient concentration of dye terminator was added to the sequencing reaction, no dideoxy-terminated fragments were formed, and all that was seen on the sequencing gel were products formed by "false stops" that were labeled with the first dye only. As used herein the term "false stops" refer to primer extension products not terminating in a dideoxy terminator, such products probably being formed when the polymerase enzyme spontaneously disengages with the template strand. When too much terminator was used, only short termination products were formed, i.e., less than about 50 nucleotides in length, such products including both the first and second dyes. When the proper amount of terminator was used, a full sequencing ladder was produced, each fragment of the ladder being labeled with both the first and second dyes.

The dye-terminator reactions were performed using AMPLITAQ™ DNA Polymerase, FS following protocols provided in the ABI PRISM™ Dye Terminator Cycle Sequencing Core Kit Manual (PE Applied Biosystems p/n 402116). (The FS enzyme is a recombinant *Thermus aquaticus* DNA polymerase having two point mutations—G46D and F667Y). All reagents except the dNTP mix, dye labeled primers, and dye-labeled terminators were from an ABI PRISM™ Dye Terminator Core Kit (PE Applied Biosystems p/n 402117). The dNTP mix consisted of 2 mM each of dATP, dCTP, dGTP and dTTP. A premix of reaction components was prepared as shown in the following table wherein all quantities are given on a per reaction basis:

| | |
|---|---|
| 5X Buffer | 4.0 µL |
| dNTP mix | 1.0 µL |
| Template: pGEM ®-3Zf(+), 0.2 µg/µL | 5.0 µL |
| Primer: −21 M13 (forward), 0.8 pmol/µL | 4.0 µL |
| AMPLITAQ DNA Polymerase, FS | 0.5 µL |
| H$_2$O | 0.5 µL |

Reactions were assembled in 0.5 ml tubes adapted for the Perkin-Elmer 480 DNA Thermal Cycler (PE Applied Biosystems p/n N801-100). Reaction volumes were 20 µL, including 15 µL of the above reaction premix, a variable amount of dye labeled terminator, and a sufficient volume of water to bring the total reaction volume up to 20 µL. From 1 to 1000 pmol of the dye terminator was added to each reaction. 30 µL of mineral oil was added to the top of each reaction to prevent evaporation. Reactions were thermocycled as follows: 96° C. for 30 sec, 50° C. for 15 sec, and 60° C. for 4 min, for 25 cycles; followed by a 4° C. hold cycle.

All reactions were purified by spin-column purification on Centri-Sep spin columns according to manufacturer's instructions (Princeton Separations p/n CS-901). Gel material in the column was hydrated with 0.8 mL deionized water for at least 30 minutes at room temperature. After the column was hydrated and it was determined that no bubbles were trapped in the gel material, the upper and lower end caps of the column were removed, and the column was allowed to drain by gravity. The column was then inserted into the wash tubes provided in the kit and centrifuged in a variable speed microcentrifuge at 1300xg for 2 minutes, removed from the wash tube, and inserted into a sample collection tube. The reaction mixture was carefully removed from under the oil and loaded onto the gel material. Columns were centrifuged in a variable speed microcentrifuge at 1300xg for 2 minutes. Eluted samples were then dried in a vacuum centrifuge.

Prior to loading onto a sequencing gel, the dried samples were resuspended in 25 µL of Template Suppression Reagent (PE Applied Biosystems p/n 401674), vortexed, heated to 95° C. for 2 minutes, cooled on ice, vortexed again, and centrifuged (13,000xg). 10 µL of the resuspended sample was aliquoted into sample vials (PE Applied Biosystems p/n 401957) adapted for the PE ABI PRISM™ 310 Genetic Analyzer (PE Applied Biosystems p/n 310-00-100/120). Electrophoresis on the 310 Genetic Analyzer was performed with sieving polymers and capillaries specially adapted for DNA sequencing analysis (PE Applied Biosystems p/n 402837 (polymer) and p/n 402840 (capillary), or, p/n 402091 (polymer) and p/n 401821 (capillary)). In each case, the sieving polymer included nucleic acid denaturants. Samples were electrokinetically injected onto the capillary for 30 sec at 2.5 kV, and run for 2 hr at 10 to 12.2 kV with the outside wall of the capillary maintained at 42° C.

Figure 1B:
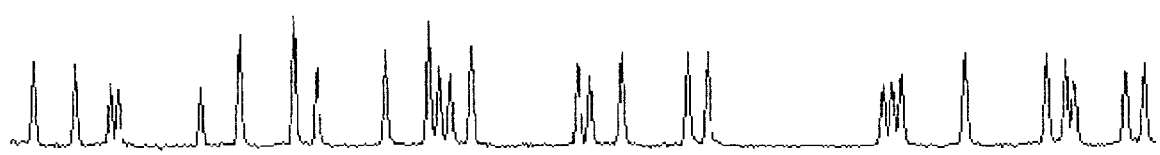
FIG. 1B shows results from a Terminator Titration Assay using 4 pmol of dye-labeled terminator.
Figure 1B:
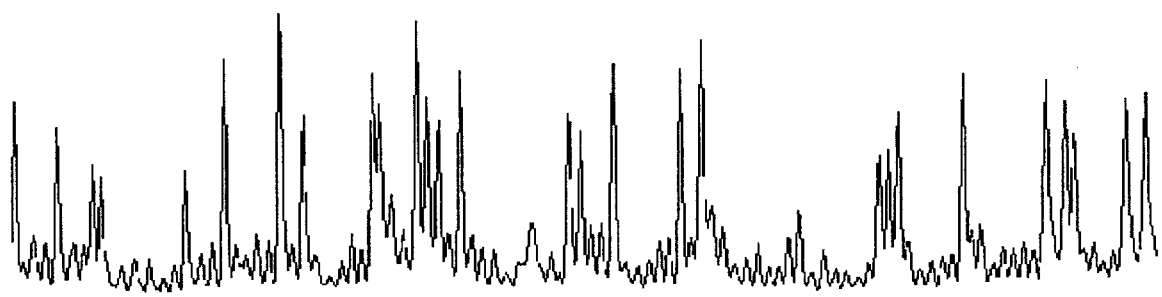
Figure 1C:
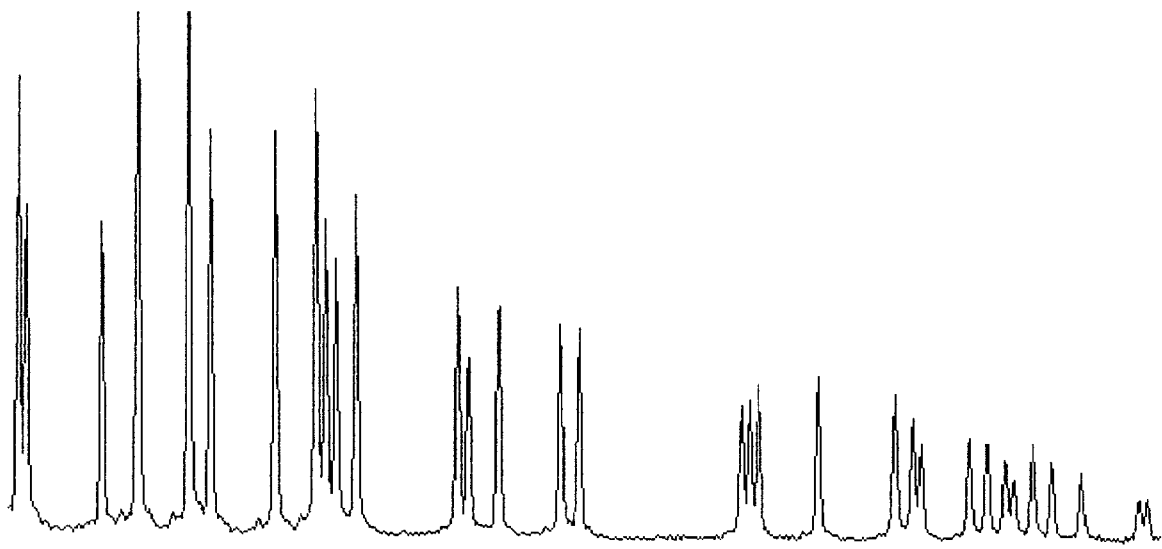
FIG. 1C shows results from a Terminator Titration Assay using 150 pmol of dye-labeled terminator.
Figure 1C:
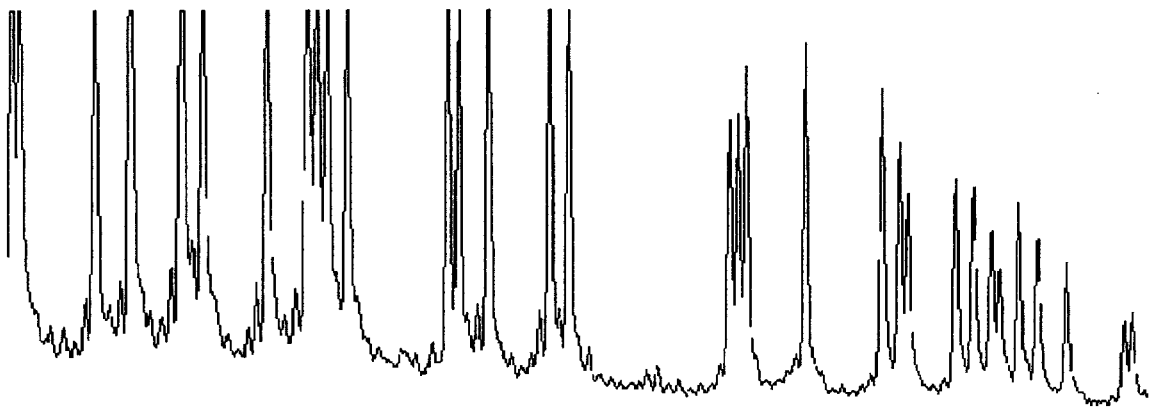

FIGS. 1A–C show typical results from a Terminator Titration Assay collected on the 310 analyzer. In each case, the dye-labeled terminator employs the traditional propargylamido linker. The traces show fluorescence intensity at a given wavelength as a function of time during an electrophoresis run for nucleotides 71–175. The amount of dye-terminator added to the primer extension reaction was variable, where in FIG. 1A 1 pmol terminator was used, in FIG. 1B 4 pmol terminator was used, and in FIG. 1C 150 pmol terminator was used. The top trace in each panel is fluorescence emitted by the dye-labeled terminator and collected at 535–545 nm and the bottom trace in each panel is fluorescence emitted from the dye-labeled primer and collected at 575–585 nm. The dye primer trace (bottom) shows false stops, i.e., fragments not terminating in a dye-labeled terminator, as well as properly terminated fragments. False stops occur when there is insufficient terminator or when a terminator is a poor polymerase substrate. The dye terminator trace (top) shows the specific incorporation of the dye-labeled terminator. The experimental conditions were as follows:

| | |
|---|---|
| Terminator: | ddATP labeled with 6-FAM at variable concentration |
| Primer: | TAMRA labeled –21M13 (forward) |
| Template: | pGEM-3Zf(+) |
| DNA Polymerase: | AMPLITAQ ™ DNA Polymerase, FS. |

FIG. 1A shows data for a reaction using 1 pmol 6-FAM-ddATP. Very little specific incorporation was detected as evidenced by the small peaks in the dye terminator trace. The false stops shown in the bottom dye-primer trace were essentially as large as any specifically-terminated peaks. This pattern indicates that the dye-terminator concentration was too low. FIG. 1B shows data for a reaction using 4 pmol 6-FAM-ddATP. Good specific terminator incorporation was observed with relatively even peak heights throughout the sequencing ladder. In the dye primer trace, easily distinguishable peaks above the false-stop noise were present, the peaks comigrating with the peaks in the dye terminator trace. This pattern indicates that the dye terminator concentration was within a useable range. FIG. 1C shows data for a reaction using 150 pmol 6-FAM-ddATP. A "top heavy" pattern was seen with the early peaks showing very high levels of dye terminator incorporation and the later peaks showing much lower levels of incorporation. This pattern indicates that the dye-terminator concentration was too high.

Figure 2:
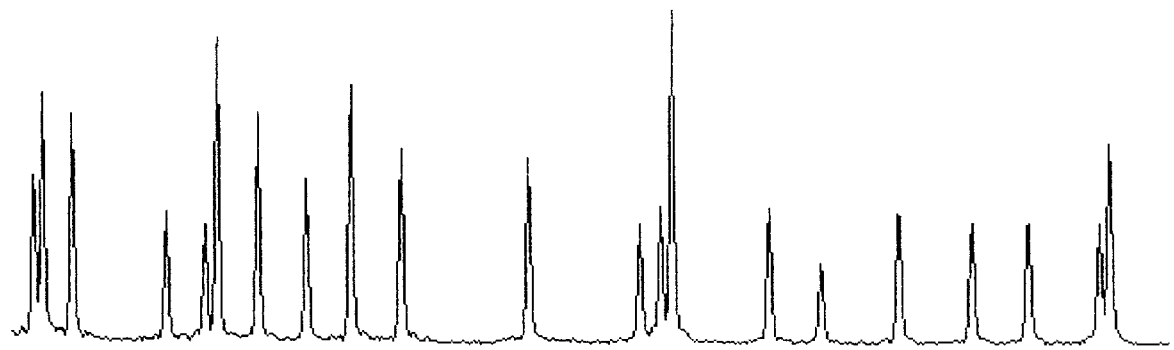
FIG. 2 shows a comparison of sequencing patterns obtained using conventional dye-labeled terminators and dye-labeled terminators of the invention.
Figure 2:
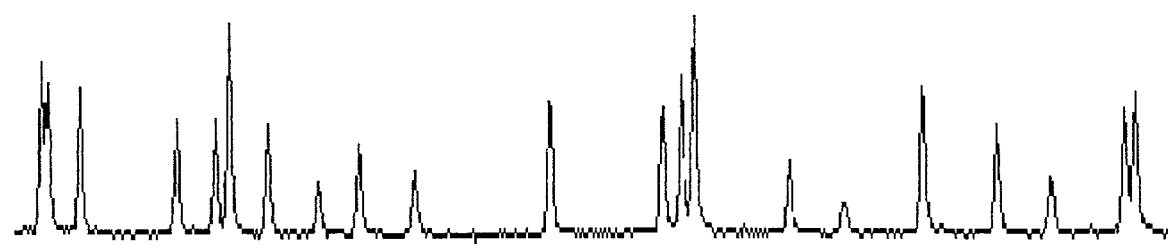

FIG. 2 shows a comparison of the sequencing patterns obtained for 6-FAM-ddCTP terminators using the propargylamido linker at a concentration of 250 pmol (top trace) and for 6-FAM-ddCTP terminators using the propargyl-1-ethoxyamido linker of the invention at a concentration of 50 pmol (bottom trace). These concentrations were determined to be the optimal concentration for each type of terminator. For the 6-FAM-ddCTP terminator using the propargylamido linker, the mean peak height was 1800, and the standard deviation was 959, resulting in a relative error of 0.533. For the 6-FAM-ddCTP terminator using the propargyl-1-ethoxyamido linker of the invention, the mean peak height was 504, and the standard deviation was 220, resulting in a relative error of 0.436. The lower relative error obtained when using the propargyl-1-ethoxyamido linker indicates a more even peak height distribution, which facilitates base-calling in an automated DNA sequencing system.

Example 2

Amount of FAM-Labeled C-Terminator

Required to Form a Full Sequencing Ladder as a Function of Linker Type The table below shows the relative molar excess of dye-labeled C-terminator required to form a full sequencing ladder according to the Terminator Titration Assay as described above in Example 1. The relative molar excess is defined such that the amount of unlabeled dideoxy terminator required to form a full sequencing ladder results in a value of 1. In each case a C-terminator was linked to a 6-FAM dye. As can be seen from the table, the C-terminator employing the propargyl-1-ethoxyamido linker requires a six-fold reduced molar excess as compared with terminators employing the traditional propargylamido linker (9 vs 55) and a five-fold reduced molar excess as compared with terminators employing a propargyl-2-ethoxyamido linker (9 vs 45).

| Linker Arm | [a]Relative Molar Excess Terminator Required |
|---|---|
| Unlabeled terminator | 1 |
| Propargylamido | 55 |
| Propargyl-1-ethoxyamido | 9 |
| Propargyl-2-ethoxyamido | 45 |

[a]The relative molar excess is defined such that the amount of unlabeled dideoxy terminator required to form a full sequencing ladder results in a value of 1.

Example 3

Relative Molar Excess of FAM-Labeled C-Terminator Required to Form a Full Sequencing Ladder as a Function of Linker Type and Dye The table below compares the relative molar excess of dye-labeled C-terminator required to form a full sequencing ladder according to the Terminator Titration Assay as described above in Example 1 for various combinations of dyes and linkers. The relative molar excess is defined as above. As can be seen from the table, the C-terminator employing the propargyl-1-ethoxyamido linker results in from a six-fold to a two-fold reduction in molar excess as compared with terminators including existing propargylamido linkers, depending on the particular dye used.

| Linker Type | Dye | Relative Molar Excess Terminator Required |
|---|---|---|
| None | None | 1 |
| Propargylamido | 6-FAM | 55 |
| Propargyl-1-ethoxyamido | 6-FAM | 9 |
| Propargylamido | HEX-2 | >250 |
| Propargyl-1-ethoxyamido | HEX-2 | 45 |
| Propargylamido | HEX-1 | 25 |
| Propargyl-1-ethoxyamido | HEX-1 | 12 |
| Propargylamido | FLAN-2 | 60 |

-continued

| Linker Type | Dye | Relative Molar Excess Terminator Required |
|---|---|---|
| Propargyl-1-ethoxyamido | FLAN-2 | 12 |
| Propargylamido | TET-2 | 60 |
| Propargyl-1-ethoxyamido | TET-2 | 20 |

Example 4

Single Nucleotide Incorporation Assay for Measuring Relative Enzyme Selectivity

A. General Description of the Assay

The assay described in this Example measures the preference that a DNA polymerase shows for a non-dye-labeled terminator over a dye-labeled terminator for the purpose of quantifying the effect of different terminator-dye linker arm structures on terminator incorporation. In the assay, an unlabeled terminator and its cognate dye-labeled terminator are present in equal concentrations and allowed to compete for the same polymerase-substrate binding site under enzyme limited (steady-state) conditions.

Figure 3:
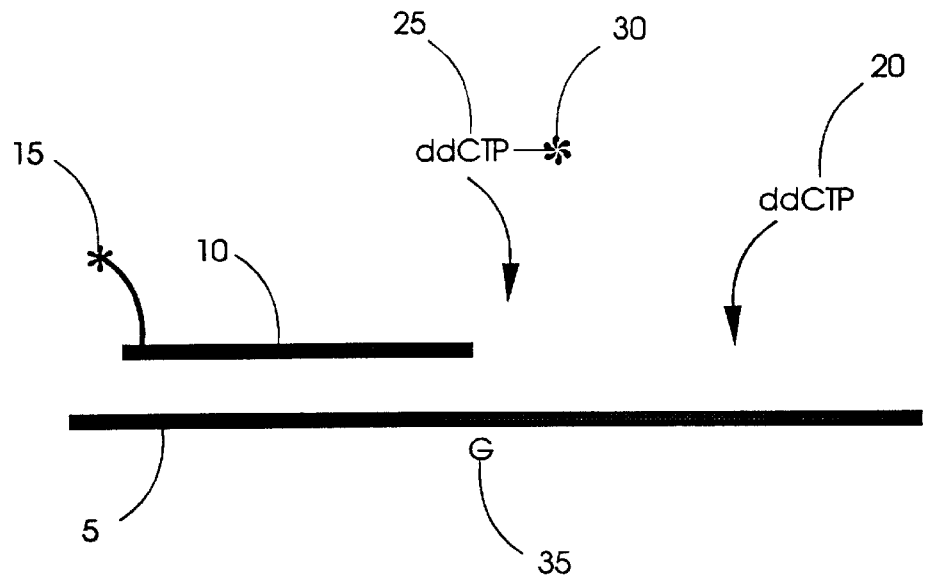
FIG. 3 shows a diagram of the Single Nucleotide Incorporation Assay used to characterize the dye-labeled terminators of the invention.
Figure 3:
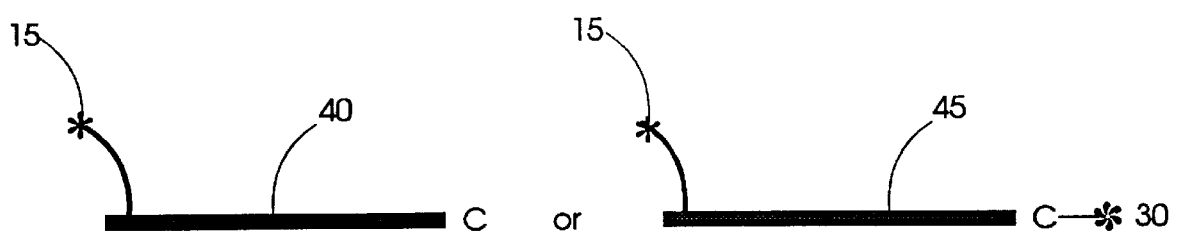

With reference to FIG. 3, the components of the assay include a 36 nucleotide template (5); a 25 nucleotide primer (10) having a sequence complementary to the template and a first fluorescent label at the 5'-end (15); an unlabeled terminator (20); a dye-labeled terminator (25) having a second fluorescent label attached thereto (30) which is spectrally resolvable from the first fluorescent label; and a polymerase enzyme. In the present example, the unlabeled terminator was 2',3'-ddCTP and the dye-labeled terminator was 6-(FAM-ddCTP where different linker arms were used to attach the dye to the nucleotide. The template DNA contained a single G (35) at the template position following the end of the primer. Incorporation of the unlabeled terminator (20) resulted in the formation of a 26-base long primer-product ending in ddC (40), while incorporation of the dye-labeled terminator resulted in the formation of a 26-base long primer-product ending with a (FAM)-ddC (45).

Products (40) and (45) were detected by resolving them electrophoretically and detecting the resulting bands using an ABI PRISM™ 373 DNA Sequencer (PE Applied Biosystems). A typical banding pattern consisted of a 25-mer band corresponding to the labeled primer (10), a 26-mer band corresponding to the product (40) and an "apparent 27-mer" which corresponded to product (45). The apparent extra base seen in product (45) is a result of the effect of the dye-labeled terminator on the electrophoretic mobility of the fragment. By taking samples from a reaction mixture and measuring the relative amounts of DNA in the 25-mer, 26-mer, and apparent 27-mer bands as a function of time, it was possible to measure the relative incorporation rates of the unlabeled and dye-labeled terminators in the reaction. After correcting for dye energy transfer (see below), the ratio of rates of incorporation was found to be a direct measure of the enzyme's preference for an unlabeled terminator over a dye-labeled terminator. In this manner, it was possible to measure the effect of linker structure on dye-terminator incorporation.

B. Energy Transfer Correction

For the case of product (45), it is necessary to correct the fluorescence signal for fluorescence energy transfer which takes place between the first fluorescent label (15) located at the 5'-end of product (45), TAMRA in this example, and the second fluorescent label (30) located on the terminator positioned at the 3'-end of product (45), FAM in this example. Under the conditions used for detection, the presence of the 3'-FAM label serves to enhance the signal resulting from the TAMRA label. The energy-transfer correction is accomplished by synthesizing a doubly labeled internal standard molecule having the same structure as product (45), preparing a control sample containing equal moles of the 5'-TAMRA labeled primer (10) and the doubly labeled internal standard molecule, and running the control sample in a control lane on the same gel as assay products (40) and (45). Any difference in TAMRA fluorescence between the primer (10) and the doubly labeled internal standard is a quantitative measure of the extent of energy transfer between the dye moieties in the assay product (45). For example, for equal moles of primer (10) and doubly labeled internal standard, the TAMRA fluorescence from the internal standard is typically 1.6x to 1.7x higher than the TAMRA-fluorescence from the primer (10), suggesting that the FAM moiety transfers energy to the TAMRA dye in the internal standard, resulting in artificially high TAMRA fluorescence. This measurement was used to correct the TAMRA fluorescence from the product (45) in each of the test sample lanes.

C. Reaction Conditions

The reaction conditions used to measure the bias that a mutant form of Taq DNA polymerase ("AMPLITAQ FS") shows for ddCTP over FAM-ddCTP are provided in the table below. (The numbers in parenthesis next to certain components refer to elements in FIG. 3.)

| Component | Final Concentrations |
|---|---|
| TRIS.Cl, pH 9.0 at 20° C. | 80 mM |
| 5' TAMRA-Labeled Primer (10) | 1000 nM |
| Template (5) | 1000 nM |
| MgCl$_2$ | 2.4 mM |
| ddCTP (20) | 200 µM |
| FAM-ddCTP(25) | 200 µM |
| AMPLITAQ ™ FS Polymerase | 8 nM |
| Reaction Temperature | 60° C. |

The assay reactions were prepared as follows. Two 2x-concentrated "Half Reaction Mixtures" were prepared and held on ice. A first solution, the "2x Enz.DNA" mixture, comprised 2000 nM template/primer DNA and 16 nM AMPLITAQ FS in 80 mM TRIS buffer. A second solution, the "2x Mg.Nuc" mixture, comprised 80 mM TRIS buffer plus 4.8 mM MgCl$_2$ and each of the nucleotides at 400 µM. A "Zero Time Control" sample was prepared by adding 1 µl of the 2x Enz.DNA mixture to 25 µl of "STOP Solution" (0.5M EDTA, °C.), and, after mixing, adding 1 µl of the 2x Mg.Nuc mixture. The Zero Time Control sample was held on ice until the remainder of the timed samples were also collected for further processing.

The remainder of each Half Reaction Mixture was pre-incubated for 5 minutes at 60° C., and the assay reaction was started by adding an equal volume of the 2x Mg.Nuc mixture to the 2x Enz.DNA mixture. At appropriate time points (in this example, at 20 second intervals), samples were removed (2 µl each) and rapidly quenched in 25 µl of the ice cold STOP Solution. A total of 10 samples were collected ranging over an elapsed time of about 200 s.

To prevent overloading of the detector in the Model 373 DNA Sequencer, samples were further processed to remove excess unincorporated FAM-ddCTP. This was accomplished by lithium chloride-ethanol precipitation using tRNA as a carrier. 5 μl of a quenched sample was added to 250 μl of "PPT Solution" (consisting of 0.8M LiCl plus 0.2 g/ml *E. coli* tRNA). After mixing, 750μl of 95% ethanol was added. Each sample was mixed and held on ice for 30 to 60 minutes to precipitate the primer/template DNA.

To prepare samples for loading onto the 373, the LiCl/Ethanol precipitate was pelleted at 10,000 x g in a microcentrifuge for 5 minutes and the supernatant fluid was removed by vacuum aspiration. After 5 minutes air drying, 50 μl of "Gel Sample Solution" (50% formamide plus 3% dextran blue) was added. Pellets were dissolved by vigorous mixing and heating at 95° C. for 3 minutes, after which 3 μl of each sample was loaded into separate lanes of a 16% denaturing, polyacrylamide sequencing gel (ABI PRISM™ 373 DNA Sequencing System User's Manual). Electrophoresis running conditions were 2600 V, 50 mA, 100 mW. Detection of the fluorescent signal in each of the bands was accomplished using GeneScan™ software (PE Applied Biosystems, p/n 672-30).

D. Quantitation of Data

A "Control Lane" was loaded with 3 μl of Gel Sample Solution containing 10 fmol of TAMRA-labeled primer and 10 fmol of double dye-labeled internal standard. The amount of TAMRA fluorescence was determined for the 25-mer band and compared to the TAMRA signal in the internal standard band. In this case, as mentioned above, the TAMRA signal from the internal standard was 1.6x higher than the TAMRA signal from he primer band. Therefore, the TAMRA signal in each of the assay product (45) bands as multiplied by a 1/1.6 correction factor.

The relative amounts of DNA in each of the bands for a given lane was calculated by dividing the fluorescence units in each of the bands by the total number of units for that lane and multiplying that figure by the concentration of the DNA primer/template in the reaction. This normalized the signal in each of the lanes to the total DNA concentration in the reaction and corrected for lane-to-lane variation due to gel-loading artifacts.

To determine the rate of incorporation of each of the nucleotides, the amounts of DNA in each of the bands was plotted versus time and the linear portions of each curve were fitted using a linear least squares fitting program. The rate of incorporation was calculated for the unlabeled ddC as the rate of appearance of the 26-mer assay product (40), while the rate of incorporation of FAM-ddC was calculated as the rate of appearance of the apparent 27-mer assay product (45). The ratio of these rates represented the preference that the DNA polymerase showed for ddCTP over FAM-ddCTP.

E. Results

Figure 4:
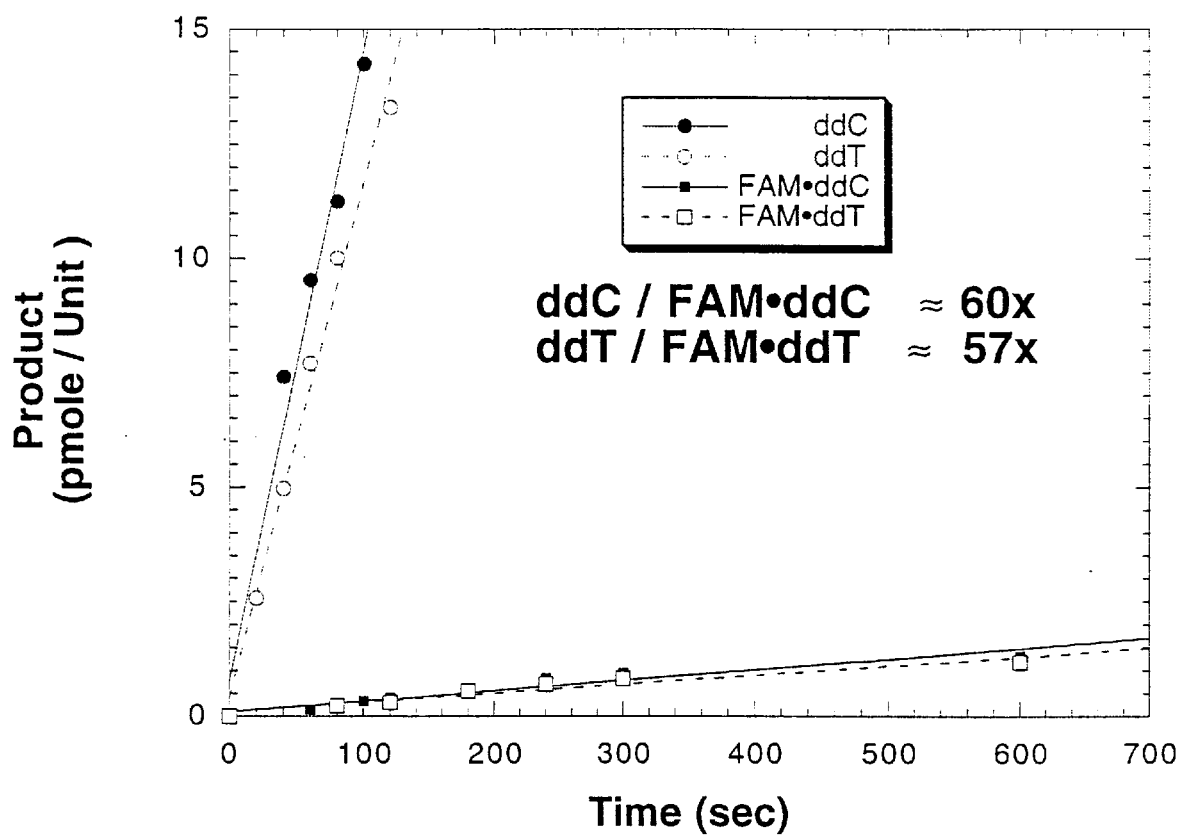
FIG. 4 shows results from the Single Nucleotide Incorporation Assay comparing the rates of incorporation of unlabeled and dye-labeled terminators.

FIG. 4 shows representative data comparing the incorporation rates of unlabeled and dye-labeled terminators. The data in the figure were corrected for energy transfer effects as discussed above. The linker used was the propargylamido linker.

The data in the table below indicate that there is a preference for unlabeled ddCTP over any of the dye-labeled derivatives tested irrespective of the particular dye or linker used. However, the magnitude of this preference is strongly dependent upon the type of linker-arm used to attach the dye to the base. In the case of the traditional propargylamido linker, ddCTP is preferred 65x more than FAM-ddCTP and over 800x more than HEX-ddCTP. When the linker arm is extended by only 3 atoms (an ether oxygen and two methylene carbons, i.e., the propargyl-1-ethoxyamido linker), the bias against FAM-ddCTP is reduced from 65x to 19x and for HEX-ddCTP from over 800x to only about 4x, a decrease by a factor of over 200. Inserting two ether units (i.e., the propargyl-2-ethoxyamido linker) between the propargyl linker and the dye, however, has a deleterious effect, increasing the bias against FAM-ddCTP about 2-fold (from 65x to 110x).

| (Dye)-linker | ddCTP/(Dye)-ddCTP |
|---|---|
| (6-FAM)-propagylamido-C | 65x |
| (6-FAM)-propagyl-1-ethoxyamido-C | 19x |
| (6-FAM)-propagyl-2-ethoxyamido-C | 110x |
| (HEX)-propagylamido-C | >800x |
| (HEX)-propagyl-1-ethoxyamido-C | 4x |

Example 5

Synthesis of 5-{3-(2-Aminoethoxy)propyn-1-yl}-2', 3'-dideoxycytidine triphosphate (13)

Materials and Methods

Thin layer chromatography (TLC) was conducted on glass plates precoated with 250 μm layers of silica gel 60-F$_{254}$ Compounds were located on the TLC plate after developing by quenching of fluorescence and/or by charring with 5% sulfuric acid. Flash column chromatography was performed on SIP brand silica gel 60 Å, 230–400 Mesh ASTM (Baxter Scientific p/n C4582-87). NMR spectra were obtained as follows: $^1$H NMR spectra were recorded at 300 MHz on solutions in CDCl$_3$ (internal Me$_4$Si, δ0) or D$_2$O (external Me$_4$Si δ0) at ambient temperature; $^{13}$C NMR spectra were recorded at 75.5 MHz on solutions in CDCl$_3$ (internal Me$_4$Si, δ0); $^{19}$F NMR spectra were recorded at 282.23 MHz on solutions in CDCl$_3$ or D$_2$O (external CFCl$_3$, δ0); and $^{31}$P NMR spectra were recorded at 121.44 MHz on solutions in D$_2$O. In all cases, NMR data were in accord with the proposed structures. Unless otherwise indicated, all reactions were carried out at ambient temperature, and in the work-up, solutions in organic solvents were washed with equal volumes of aqueous solutions. Organic solutions were generally dried over anhydrous Na$_2$SO$_4$ prior to concentration on a rotary evaporator under vacuum with a bath temperature of 40°–50° C. The HPLC systems used for analytical and preparative purposes were as follows:

Analytical reverse-phase HPLC: column: Spheri-5 RP-C18, 5 μm particle size, 220×4.6 mm (PE Applied Biosystems p/n 0711-0017); gradient: 0 to 50% acetonitrile at 1.5. ml/min over 20 min, followed by 50% acetonitrile to 100% acetonitrile at 1.5 ml/min over 10 min.

Analytical ion pair HPLC: column: AQUAPORE-OD-300 ion-pair chromatography column, 7 μm particle size, 220×4.6 mm (PE Applied Biosystems p/n 0711-0331); gradient: 0 to 40% acetonitrile at 1.5 ml/min over 30 min, followed by 40% acetonitrile to 60% acetonitrile at 1.5 ml/min over 5 min.

Preparative anion exchange HPLC: column: AQUAPORE™ anion ion-exchange chromatography column, 20 μm particle size, 250×10 mm (PE Applied Biosystems p/n 0711-0172); gradient: 40% acetonitrile:60% 100 mM TEAB, pH 7.0 to 40% acetonitrile:60% 1.5 mM TEAB pH 8 at 4.5 ml/min over 20 min, followed by isocratic elution.

Preparative reverse phase HPLC: column: Prep Nova Pak HR-C18, 6 μm particle size, 60 Å pore size, 300×40 mm (Waters Division of the Millipore Corporation p/n WAT037704); gradient (for mono and triphosphates): 100%

100 mM TEAB pH 7 to 20% acetonitrile:80% 100 mM TEAB pH 7 at 50 ml/min over 30 min, followed by 20% acetonitrile:80% 100 mM TEAB pH 7 to 50% acetonitrile:50% 100 mM TEAB pH 7 over 10 min; gradient (for dye-labeled triphosphates): 100% 100 mM TEAB pH 7 to 10% 100 mM TEAB pH 7: 90% acetonitrile.

B. Synthesis of 2-Phthalimidoethanol (3)

Figure 5:
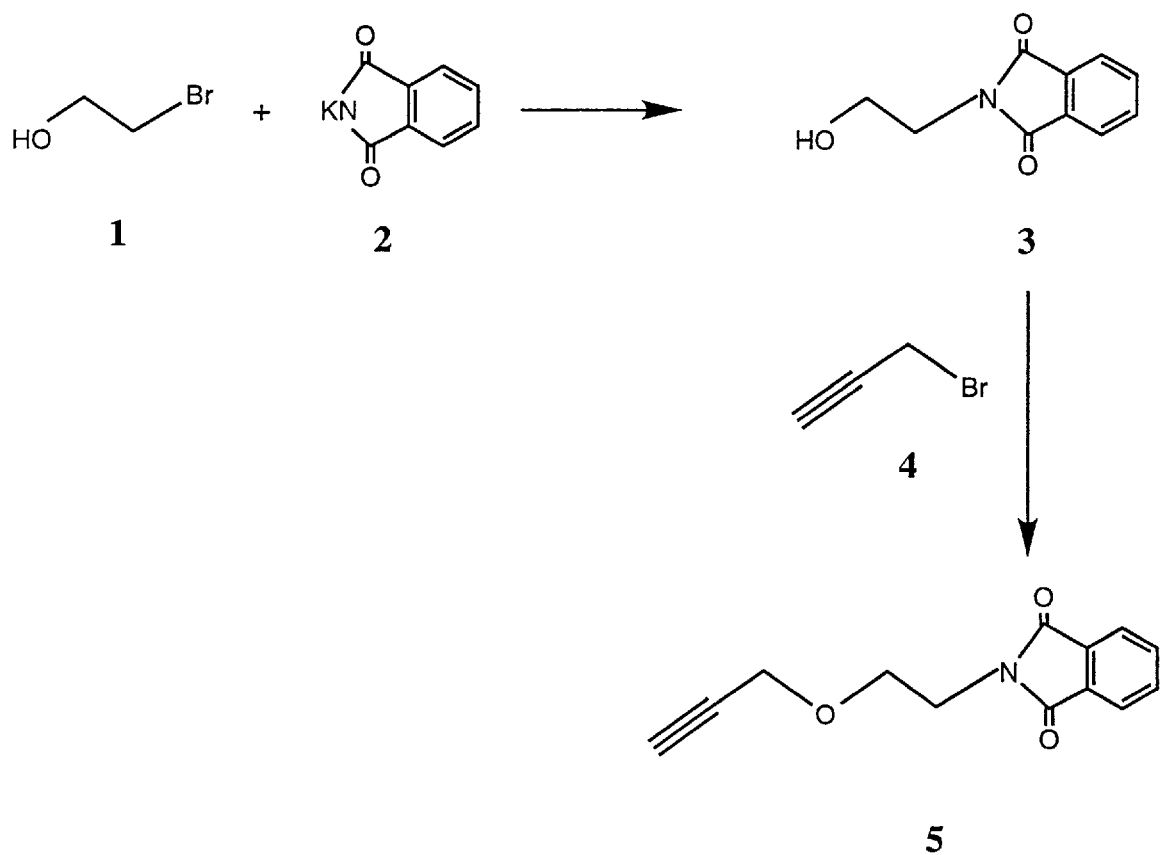
FIG. 5 shows the synthesis of 2-phthalimidoethanol (3) and 3-(2-phthalimidoethoxy)propyne (5).

Potassium phthalimide 2 (2.7 g, 14.6 mmol) was added to a solution of bromoethanol 1 in N,N-dimethylformamide (12 mL, 14.1 mmol). After stirring for 12 h at 70° C., the mixture was concentrated and then diluted with dichloromethane (100 mL). After removal of solids by filtration, the organic layer was washed with water, dried, and concentrated. The concentrate was purified by flash column chromatography (3:2 to 2:3 hexane-ethyl acetate) to give compound 3 as a white solid (1.19 g, 44.12%) having an $R_F$ of 0.22 (3:2 hexane-ethyl acetate). See FIG. 5.

C. Synthesis of 3-(2-Phthalimidoethoxy)propyne (5)

To a stirred solution of compound 3(1.14 g, 5.96 mmol) in N,N-dimethylformamide (20 mL) was added NaH (0.36 g, 80%) dropwise. After complete NaH addition, stirring was continued for 0.5 h at room temperature, and then the reaction was cooled to 0° C. Propargyl bromide 4 (1.5 mL, 13.47 mmol) was added, and the stirring was continued for an additional 0.5 h at 0° C., then, at room temperature for 2 h. After careful addition of methanol to decompose excess NaH, the solvent was evaporated and the crude product was purified by flash column chromatography (3:2 to 1:1 to 2:3 hexane-ethyl acetate) to give compound 5 as a solid (495 mg, 36.2%) having an $R_F$ of 0.22 (3:2 hexane-ethyl acetate). See FIG. 5.

D. Synthesis of 5-{3-(2-Phthalamidoethoxy)-propyn-1-yl}-2',3'-dideoxycytidine (7)

Figure 6:
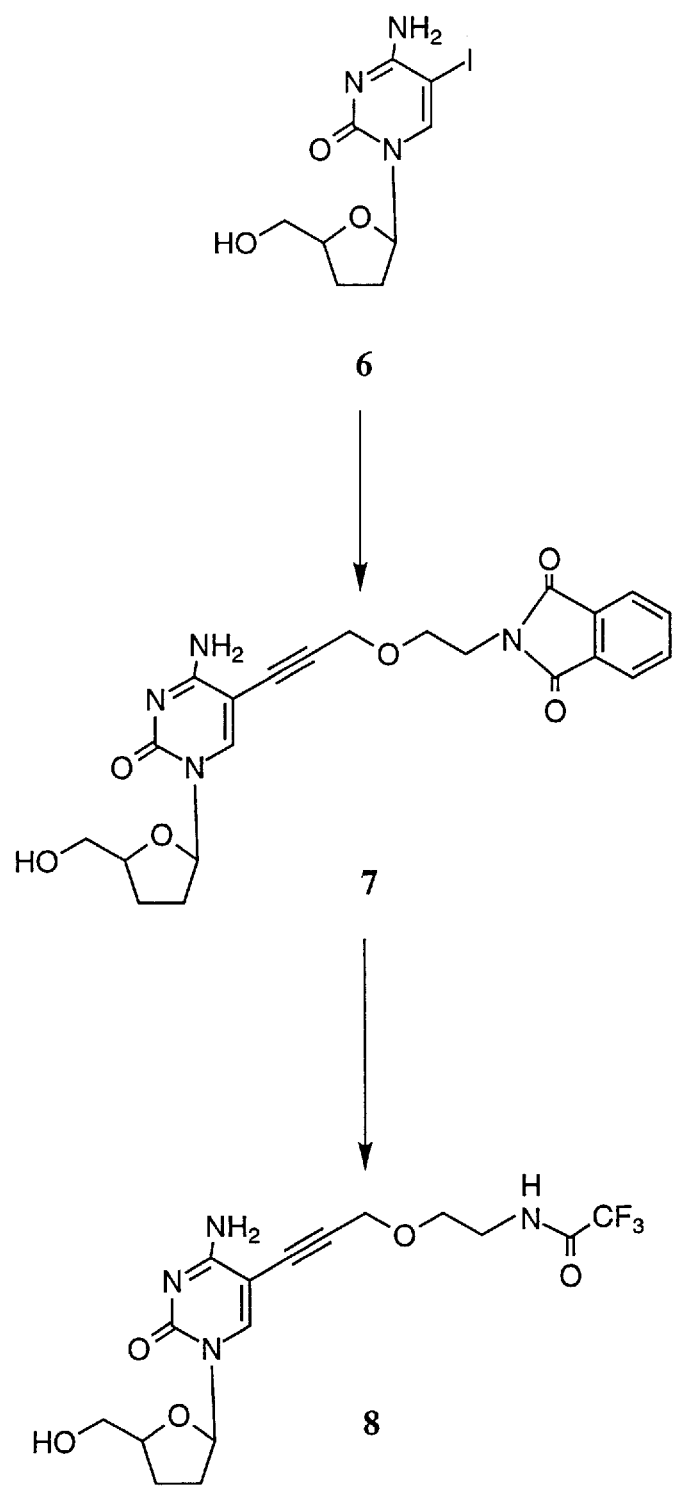
FIG. 6 shows the synthesis of 5-{3-(2-phthalamidoethoxy)-propyn-1-yl}-2',3'-dideoxycytidine (7) and of 5-{3-(2-trifluoroacetamidoethoxy)propyn-1-yl}-2',3'-dideoxycytidine (8).

5-Iodo-2',3'-dideoxycytidine 6 (100 mg, 0.3 mmol) was reacted with compound 5 (158 mg, 0.69 mmol) in the presence of cuprous iodide (11.4 mg, 0.06 mmol), tetrakis (triphenylphosphine)palladium (69 mg, 0.06 mmol), and triethylamine (84 µL, 0.6 mmol) in N,N-dimethylformamide (1 mL) for 12 h at room temperature under Argon atmosphere. The reaction was then diluted with 2 g bicarbonate form of Dowex-1 anion exchange resin in methanol. After stirring for 1 h at room temperature the reaction mixture was filtered and concentrated. The product was purified by flash column chromatography (13:1 dichloromethene-methanol) to give compound 7 (75 mg, 57.66%) having an $R_F$ of 0.23 (solvent 9:1 dichloromethane-methanol). See FIG. 6.

E. Synthesis of 5-{3-(2-Trifluoroacetamidoethoxy) propyn-1-yl}-2',3'-dideoxycytidine (8)

A mixture of compound 7 (73 mg, 0.17 mmol) and ethylenediamine (400 µL) was heated at 80° C. in ethanol (4 mL) for 1 h. The reaction was then evaporated to dryness, the residue was dissolved in N,N-dimethylformamide (2 mL), and methyl trifluoroacetate (6.5 mL) was added. After stirring for 1 h at 80° C., the solvent was evaporated and the residue was purified by flash column chromatography (9:1 dichloromethane-methanol) to give compound 8 (36 mg, 50.7%) having an $R_F$ of 0.24 (solvent 9:1 dichloromethanemethanol). See FIG. 6.

F. Synthesis of 5-{3-(2'-Trifluoroacetamidoethoxy) propyn-1-yl}-2,3'-dideoxycytidine monophosphate (10)

Figure 7:
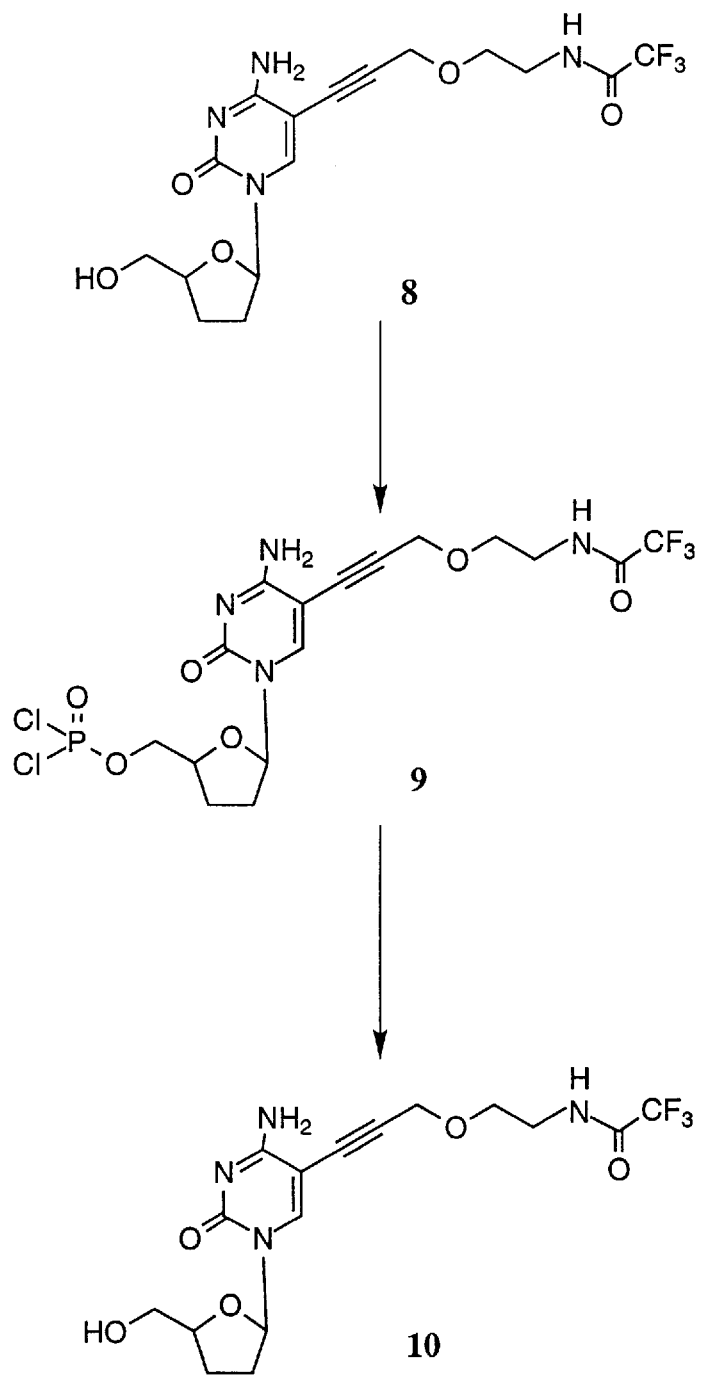
FIG. 7 shows the synthesis of 5-{3-(2'-trifluoroacetamidoethoxy)propyn-1-yl}-2',3'-dideoxycytidine monophosphate (10).

Freshly distilled phosphorous oxychloride (16.2 µL, 0.17 mmol) was added to nucleoside 8 (18.8 mg, 0.046 mmol) in trimethylphosphate (150 µL) at −30° C. to form the corresponding dichloromonophosphate 9. The reaction mixture was allowed to warm to −5° C. over a period of 80 minutes and stirring was continued for an additional 1 h at room temperature. The reaction was quenched with 2M TEAB buffer pH 8.0, and purified by preparative reverse phase HPLC as described above. Fractions corresponding to product were concentrated to give monophosphate 10 (12.3 mg, 54.56%). See FIG. 7.

G. Synthesis of 5-{3-(2-Trifluoroacetamidoethoxy) propyn-1-yl}-2',3'-dideoxycytidine triphosphate (12)

Figure 8:
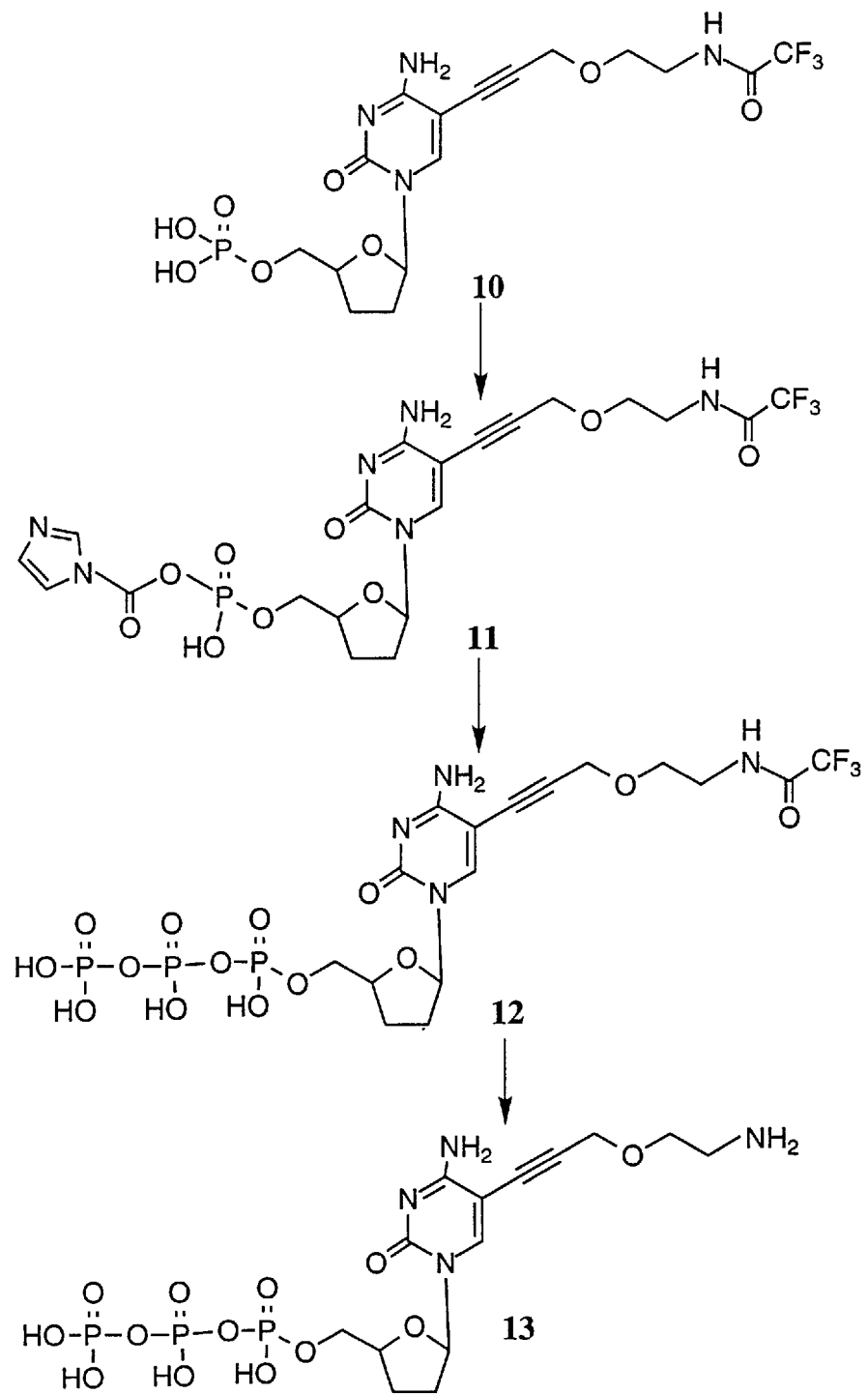
FIG. 8 shows the synthesis of 5-{3-(2-trifluoroacetamidoethoxy)propyn-1-yl}-2',3'-dideoxycytidine triphosphate (12) and 5-{3-(2-aminoethoxy)propyn-1-yl}-2',3'-dideoxycytidine triphosphate (13).

The monophosphate 10 (7.4 mg, 15.3 mmol) dissolved in N,N-dimethylformamide (200 µl) was stirred with carbonyldiimidazole (CDI) (4.2 mg, 25.9 mmol) for 1 h at room temperature. Excess CDI was quenched by the addition of dry methanol (40 µL). The activated monophosphate 11 was stirred with a solution of tributylammonium pyrophosphate in N,N-dimethylformamide (160 µL) containing n-tributylamine (16 µL) for 24 h at room temperature. The reaction was quenched with 2M TEAB pH 8.0 and purified by preparative reverse phase HPLC as described above. The fractions corresponding to product were concentrated to give triphosphate 12. See FIG. 8.

H. Synthesis of 5-{3-(2-Aminoethoxy)propyn-1-yl}-2',3'-dideoxycytidine triphosphate (13)

The purified protected triphosphate 12 was taken up in concentrated aqueous $NH_4OH$ (4 mL) and stirred for 2.5 h at room temperature. The reaction mixture was concentrated to give compound 13 which was formulated with 0.1M TEAB pH 7.0 to a concentration of 2.6 mM. The concentration and purity of the formulated bulk were confirmed by UV/Vis spectroscopy and analytical ion pair HPLC as described above, respectively. See FIG. 8.

Example 6

Synthesis of 5-[3-{2-(2-Aminoethoxy) ethoxy}propyn-1-yl]-2',3'-dideoxycytidine triphosphate (23)

A. Materials and Methods

The materials and methods were essentially the same as described above with respect to Example 5.

B. Synthesis of 2-(2-Phthalimidoethoxy)ethanol (15)

Figure 9:
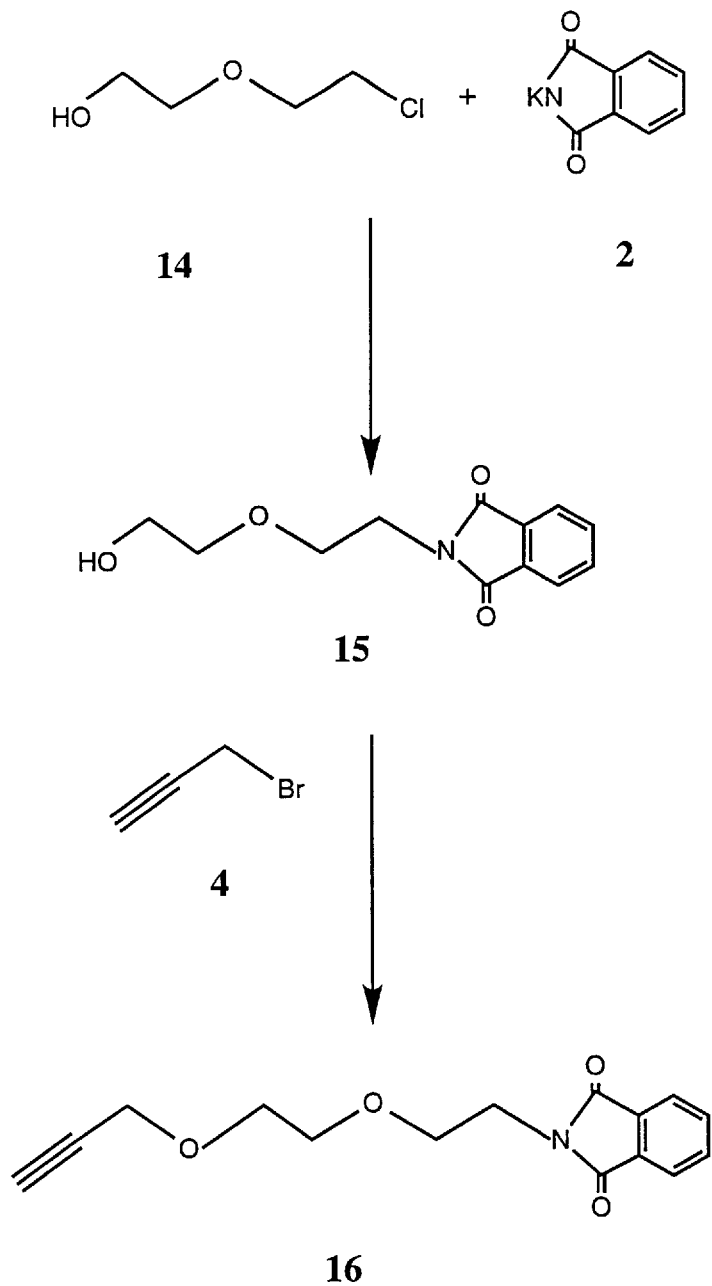
FIG. 9 shows the synthesis of 2-(2-phthalimidoethoxy)ethanol (15) and 3-[2-(2-phthalimidoethoxy)ethoxy]propyne (16).

To a solution of 2-(2-chloroethoxy)ethanol 14 (5 mL, 47.4 mmol) in N,N-dimethylformamide (35 mL) was added potassium phthalimide 2 (8.8 g, 47.51 mmol), and the reaction mixture was stirred for 20 h at 70° C. The mixture was concentrated and then diluted with dichloromethane (300 mL), and the organic layer was washed with water, dried, and concentrated. The residue was purified by flash column chromatography (3:2 to 2:3 hexane-ethyl acetate) to give compound 15 as a white solid (7.15 g, 64.17%) having an $R_F$ of 0.12 (solvent 3:2 hexane-ethyl acetate). See FIG. 9.

C. Synthesis of 3-[2-(2-Phthalimidoethoxy)ethoxy] propyne (16)

To a stirred solution of compound 15 (1.39 g, 5.91 mmol) in N,N-dimethylformamide (25 mL) was added NaH (0.33 g, 80%) dropwise. After complete NaH addition, stirring was continued for 0.5 h at room temperature and then cooled to 0° C. Propargyl bromide 4 (1.24 mL, 11.13 mmol) was added, and stirring was continued for 0.5 h at 0° C., then for 2 h at room temperature. After careful addition of methanol to decompose excess NaH, the solvent was evaporated and crude product was purified by flash column chromatography (3:2 to 1:1 to 2:3 hexane-ethyl acetate) to give compound 16 as a solid (591 mg, 36.6%) having an $R_F$ of 0.41 (solvent 3:2 hexane-ethyl acetate). See FIG. 9.

D. Synthesis of 5-[3-{2-(2-Phthalamidoethoxy) ethoxy}propyn-1-yl]-2',3'-dideoxycytidine (17)

Figure 10:
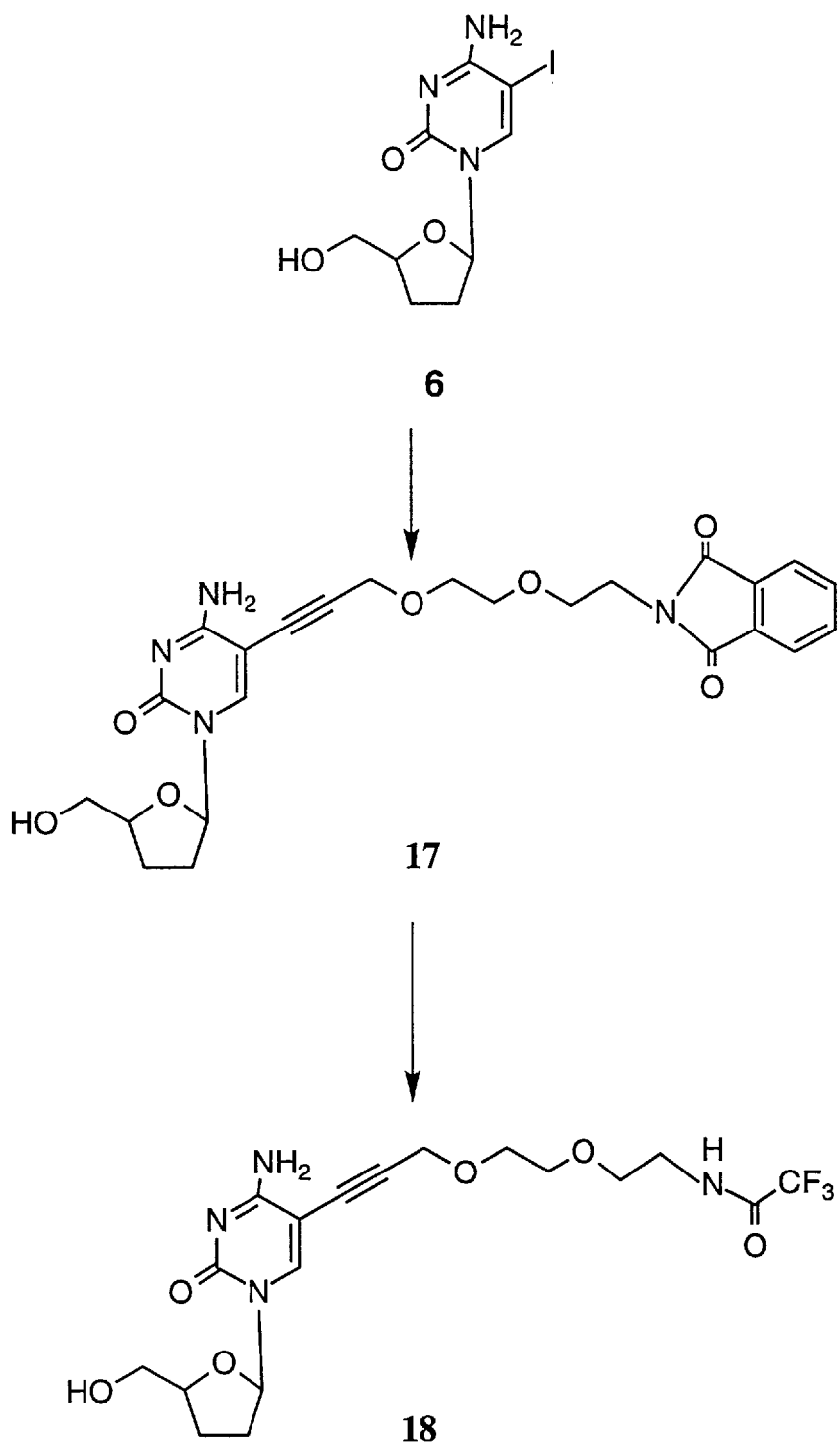
FIG. 10 shows the synthesis of 5-[3-{2-(2-phthalamidoethoxy)ethoxy}propyn-1-yl]-2',3'-dideoxycytidine (17) and 5-[3-{2-(2-trifluoroacetamidoethoxy)ethoxy}propyn-1-yl]-2',3'-dideoxycytidine (18).

5-Iodo-2',3'-dideoxycytidine 6 (240 mg, 0.71 mmol)) was reacted with compound 16 (810 mg., 2.96 mmol) in the presence of cuprous iodide (33 mg, 0.173 mmol), tetrakis (triphenylphosphine)palladium (164 mg, 0.142 mmol), and triethylamine (198 μL, 1.42 mmol) in N,N-dimethylformamide (4 mL) for 12 h at room temperature under Argon atmosphere. The reaction was then diluted with 4 g bicarbonate form of Dowex 1 anion exchange resin in methanol. After stirring for 1 h at room temperature the reaction mixture was filtered and concentrated. The product was purified by flash column chromatography (13:1 dichloromethene-methanol) to give compound 17 (245 mg, 71.3%) having an $R_F$ of 0.35 (solvent 9:1 dichloromethane-methanol). See FIG. 10.

E. Synthesis of 5-[3-{2-(2-Trifluoroacetamidoethoxy) ethoxy}propyn-1-yl]-2',3'-dideoxycytidine (18)

A mixture of compound 17 (230 mg, 0.48 mmol) and ethylenediamine (1 mL) was heated at 80° C. in ethanol (10 mL) for 1 h. The reaction mixture was then evaporated to dryness, the residue was dissolved in N,N-dimethylformamide (5 mL), and methyl trifluoroacetate (15 mL) was added. After stirring for 1 h at 80° C., solvent was evaporated and residue was purified by flash column chromatography (13:1 dichloromethanemethanol) to give compound 18 (72 mg, 33.7%) having an $R_F$ of 0.37 (solvent 9:1 dichloromethane-methanol). See FIG. 10.

F. Synthesis of 5-[3-{2-(2-Trifluoroacetamidoethoxy) ethoxy}propyn-1-yl]-2',3'-dideoxycytidine monophosphate (20)

Figure 11:
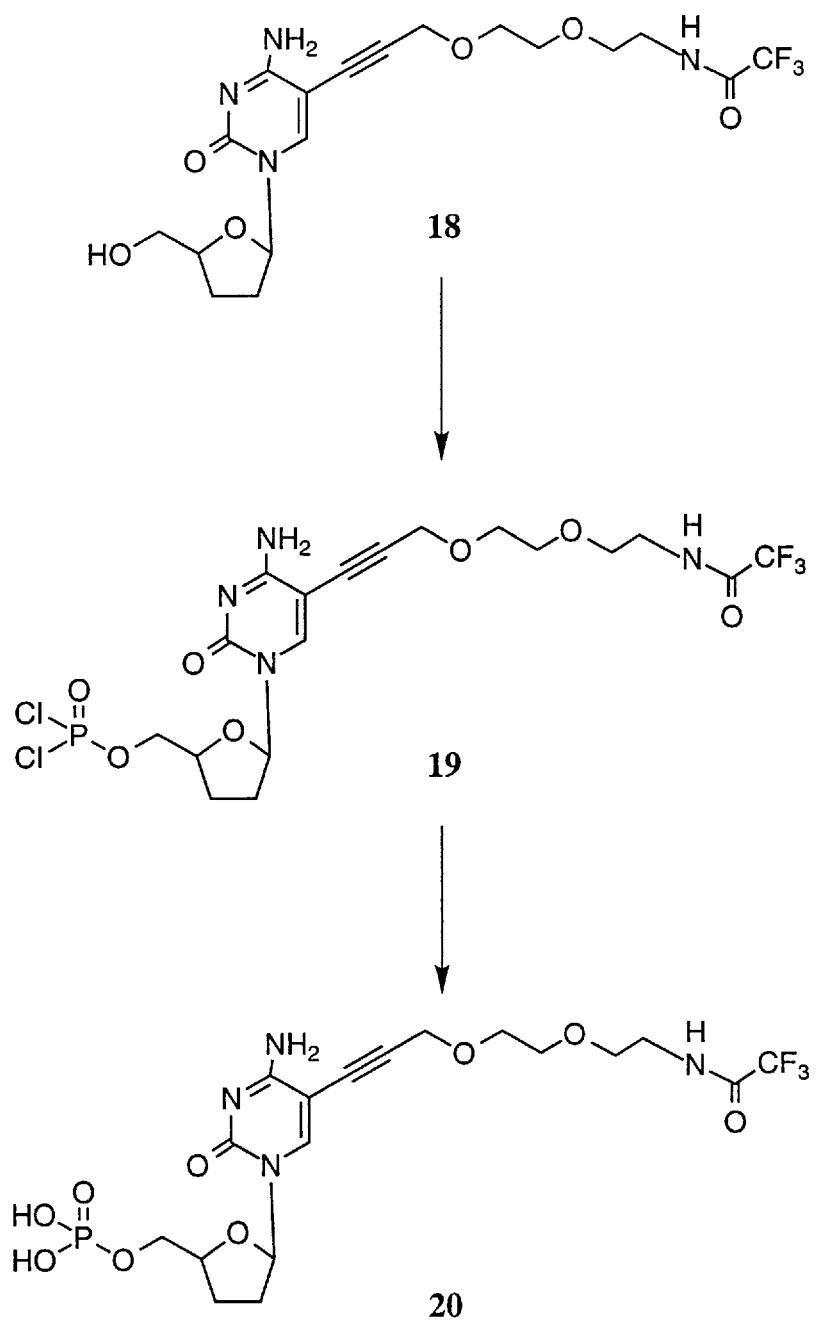
FIG. 11 shows the synthesis of 5-[3-{2-(2-trifluoroacetamidoethoxy)ethoxy}propyn-1-yl]-2',3'-dideoxycytidine monophosphate (20).

Freshly distilled phosphorous oxychloride (34.8 μL, 369 μmol) was added to nucleoside 18 (41.4 mg, 92 μmol) in trimethylphosphate (350 μL) at −30° C. to form the corresponding dichloromonophosphate 19. The reaction mixture was allowed to warm to −5° C. over a period of 80 minutes and stirring was continued for 1 h at room temperature. The reaction was quenched with 2M TEAB pH 8.0 buffer and purified by preparative reverse phase HPLC as described above. The fractions corresponding to product were concentrated to give monophosphate 20 (14.8 mg, 27.6%). See FIG. 11.

G. Synthesis of 5-[3-{2-(2-Trifluoroacetamidoethoxy) ethoxy}propyn-1-yl]-2',3'-dideoxycytidine triphosphate (22)

Figure 12:
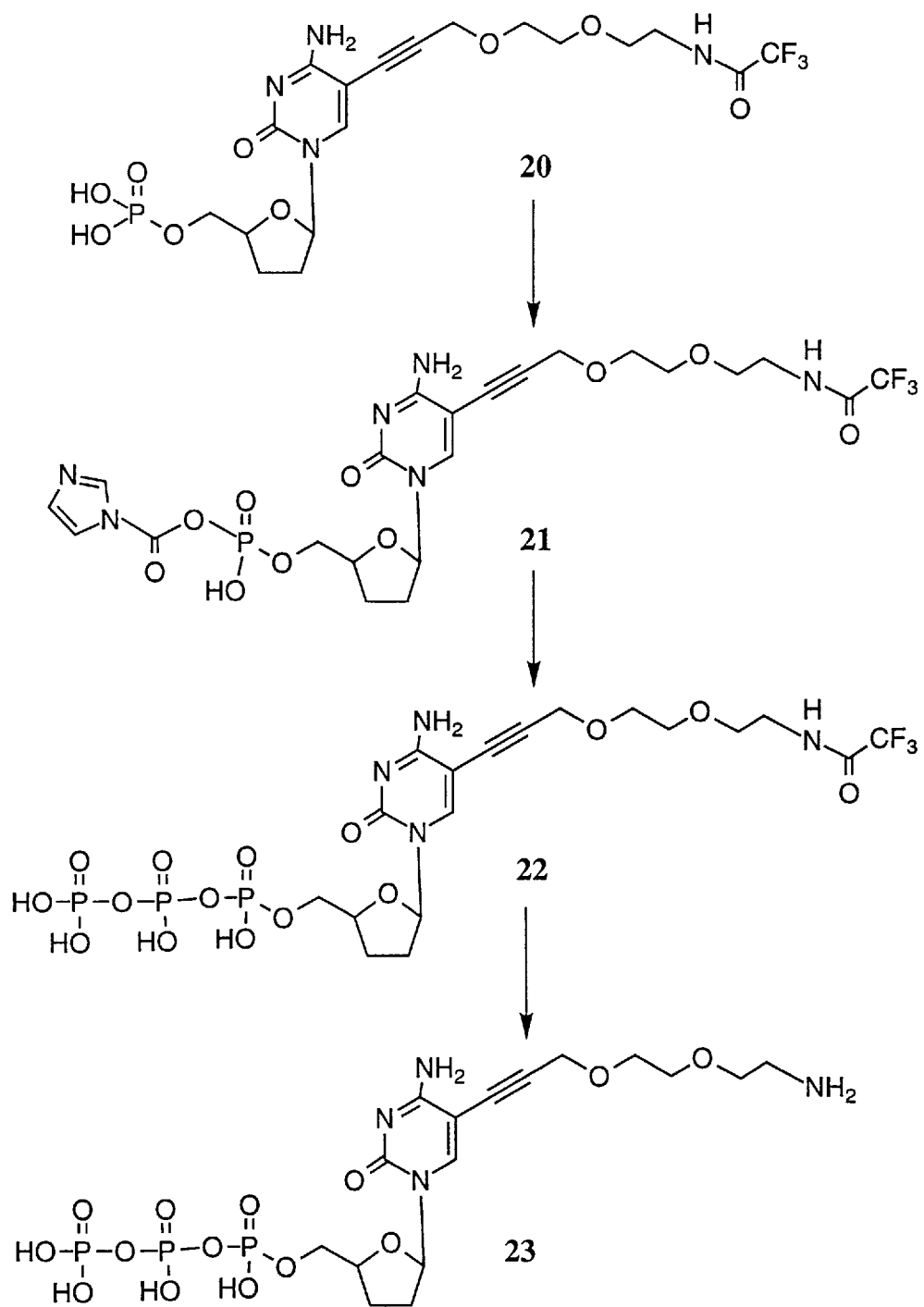
FIG. 12 shows the synthesis of 5-[3-{2-(2-trifluoroacetamidoethoxy)ethoxy}propyn-1-yl]-2',3'-dideoxycytidine triphosphate (22) and 5-[3-{2-(2-aminoethoxy)ethoxy}propyn-1-yl]-2',3'-dideoxycytidine triphosphate (23).

The monophosphate 20 (14.8 mg, 28 μmol) dissolved in N,N-dimethylformamide (300 μL) was stirred with carbonyldiimidazole (CDI) (13.5 mg, 83.26 μmol) for 1 h at room temperature. Excess CDI was quenched by the addition of dry methanol (80 μL). The activated monophosphate 21 was stirred with a solution of tributylammonium pyrophosphate (160 mg) in N,N-dimethylformamide (300 μL) containing n-tributylamine (32 μl) for 24 h at room temperature. The reaction was quenched with 2M TEAB pH 8.0 and purified by preparative reverse phase HPLC as described above. The fractions corresponding to product were concentrated to give triphosphate 22 (0.9 mg, 4.7%). See FIG. 12.

H. Synthesis of 5-[3-{2-(2-Aminoethoxy)ethoxy}propyn-1-yl]-2',3'-dideoxycytidine triphosphate (23)

The purified protected triphosphate 22 was taken up in concentrated aqueous NH$_4$OH (2 mL) and stirred for 3 h at approximately 48° C. The reaction mixture was concentrated to give compound 23 which was formulated with 0.1M TEAB pH 7.0 to a concentration of 3.5 mM. The concentration and purity of the formulated bulk were confirmed by UV/Vis spectroscopy and analytical ion pair HPLC as described above, respectively. See FIG. 12.

Example 7

Attachment of Dye to 5-{3-(2-aminoethoxy)propyn-1-yl}-2',3'-nucleotide

The nucleoside aminotriphosphate in 100 mM TEA-bicarbonate (pH 7.0) was evaporated to dryness. It was then resuspended in 250 mM bicarbonate buffer (pH 9.0). A solution of Dye-NHS (in DMSO) was added and stirred in the dark overnight at room temperature. The reaction mixture was purified by preparative anion exchange HPLC as described above. The fractions corresponding to product were concentrated and repurified by preparative reverse phase HPLC as described above. Final product was dried in vacuo and diluted with 50 mM CAPSO, pH 9.6, to a concentration of 1 mM. The concentration and purity of the formulated bulk is confirmed by UV/VIS spectroscopy and analytical ion-pairing HPLC as described above, respectively.

Example 8

Figure 13:
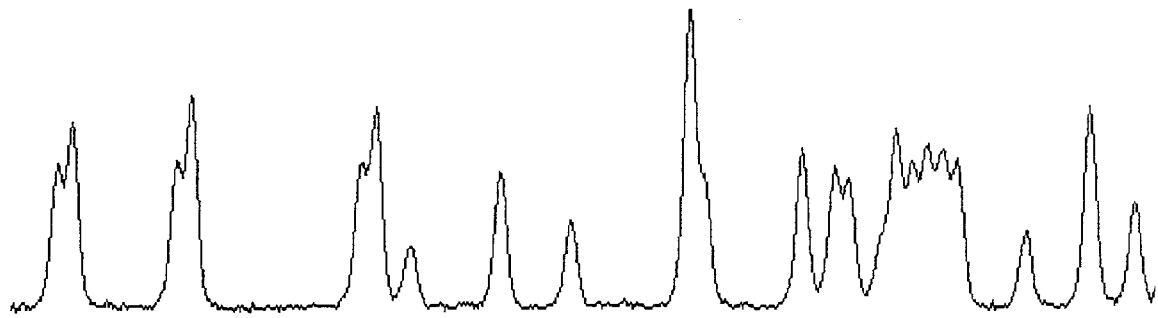
FIG. 13 shows results from a single color sequencing reaction using DTAMRA-1-labeled terminator including a propargylamido linker (top), and DTAMRA-2-labeled terminator including a propargyl-1-ethoxyamido linker (bottom).
Figure 13:
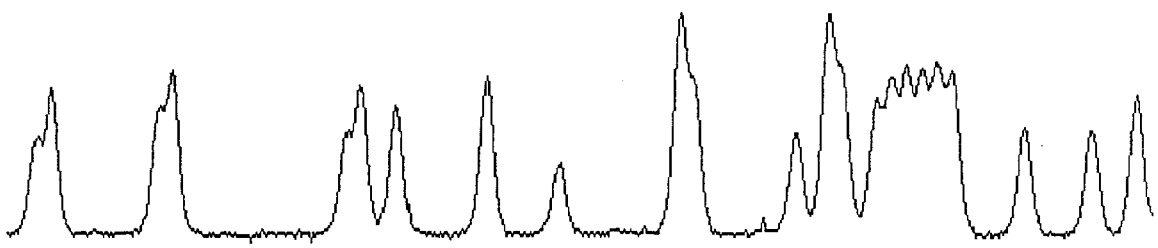

Improved Peak Height Evenness Using the Propargylethoxyamino Dideoxynucleotides of the Invention FIG. 13 shows single color sequencing reactions using dye-labeled ddCTP as the terminator. The top panel shows results using a DTAMRA-1-labeled terminator using a propargylamido linker, while the bottom pannel shows results using a DTAMRA-2-labeled terminator using an propargyl-1-ethoxyamido linker of the present invention. Different dye isomers were used to produce optimum results—the 1 isomer being the preferred compound for use with the propargylamido linker and the 2 isomer being the preferred compound for use with the propargyl-1-ethoxyamido linker. The portion of the sequencing ladder shown in FIG. 13 starts with a pair of C's at bases 495 and 496 and ends with single Cs at bases 553, 557 and 560 in the sequence of pGEM-3Zf(+) using the −21 M13 Primer (forward). In the top panel, in the group of 6 C's, the first C is present only as a leading shoulder rather than a distinct peak, while in the bottom panel, all 6 Cs are clearly resolved. The resolution of the 6 Cs in the bottom panel is made possible by the more even peak heights which are possible using the propargyl-1-ethoxyamido linker of the present invention in combination with rhodamine-type dyes. This enhanced resolution of neighboring peaks facilitates automated basecalling routines used in automated DNA sequencing systems.

All publications and patent applications are herein incorporated by reference to the same extent as if each individual publication or patent application was specifically and individually indicated to be incorporated by reference.

Although only a few embodiments have been described in detail above, those having ordinary skill in the chemical arts will clearly understand that many modifications are possible in the preferred embodiment without departing from the teachings thereof. All such modifications are intended to be encompassed within the following claims.

We claim:

1. A nucleoside compound having the structure:

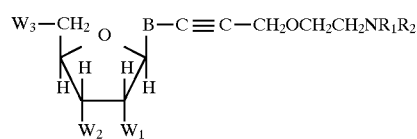

wherein:

$R_1$ and $R_2$ taken separately are selected from the group consisting of —H, lower alkyl, protecting group, and label;

B is a 7-deazapurine, purine, or pyrimidine nucleoside base;

wherein when B is purine or 7-deazapurine, the sugar moiety is attached at the $N^9$-position of the purine or deazapurine, and when B is pyrimidine, the sugar moiety is attached at the $N^1$-position of the pyrimidine; and wherein when B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine;

$W_1$ is selected from the group consisting of —H and —OH;

$W_2$ is —OH or a moiety which renders the nucleoside incapable of forming a phosphodiester bond at the 3'-position; and $W_3$ is selected from the group consisting of —$PO_4$, —$P_2O_7$, —$P_3O_{10}$, phosphate analog, and —OH.

2. The nucleoside compound of claim 1 wherein one of $R_1$ and $R_2$ is label.

3. The nucleoside compound of claim 2 wherein the label is a fluorescein-type dye.

4. The nucleoside compound of claim 2 wherein the label is a rhodamine-type dye.

5. The nucleoside compound of claim 1 wherein $W_1$ is —H and $W_2$ is —OH or a moiety which renders the nucleoside incapable of forming a phosphodiester bond at the 3'-position, and $W_3$ is —$P_3O_{10}$.

6. The nucleoside of claim 1 wherein $W_1$ is —H, $W_2$ is —OH or a moiety which renders the nucleoside incapable of forming a phosphodiester bond at the 3'-position, and $W_3$ is —$P_3O_{10}$.

7. The nucleoside compound of claim 1 wherein $W_2$ is —OH or a moiety selected from the group consisting of —H, azido, amino, fluro, and methoxy.

8. The nucleoside of claim 1 wherein B is selected from the group consisting of uracil, cytosine, 7-deazaadenine, and 7-deazaguanosine.

* * * * *